US009556486B2

(12) United States Patent
Schwinn et al.

(10) Patent No.: US 9,556,486 B2
(45) Date of Patent: Jan. 31, 2017

(54) METHODS OF IDENTIFYING INDIVIDUALS AT RISK OF PERIOPERATIVE BLEEDING, RENAL DYSFUNCTION OR STROKE

(71) Applicant: DUKE UNIVERSITY, Durham, NC (US)

(72) Inventors: Debra A. Schwinn, Durham, NC (US); Ian Welsby, Durham, NC (US); Mihai V. Podgoreanu, Durham, NC (US); Mark Stafford-Smith, Durham, NC (US); Mark F. Newman, Durham, NC (US); Hilary P. Grocott, Durham, NC (US); William D. White, Durham, NC (US); Richard W. Morris, Durham, NC (US); Joseph P. Mathew, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 14/099,718

(22) Filed: Dec. 6, 2013

(65) Prior Publication Data

US 2014/0141429 A1 May 22, 2014

Related U.S. Application Data

(63) Continuation of application No. 13/454,929, filed on Apr. 24, 2012, now abandoned, which is a continuation of application No. 12/073,113, filed on Feb. 29, 2008, now Pat. No. 8,187,807, which is a continuation of application No. 10/979,816, filed on Nov. 3, 2004, now Pat. No. 7,439,019.

(60) Provisional application No. 60/516,313, filed on Nov. 3, 2003, provisional application No. 60/567,793, filed on May 5, 2004, provisional application No. 60/620,666, filed on Oct. 22, 2004.

(51) Int. Cl.
C12Q 1/68 (2006.01)
C12P 19/34 (2006.01)

(52) U.S. Cl.
CPC ........ *C12Q 1/6883* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS

| 7,439,019 B2 | 10/2008 | Schwinn et al. |
| 7,592,141 B2 | 9/2009 | Schwinn et al. |
| 8,187,807 B2 | 5/2012 | Schwinn et al. |
| 2006/0177848 A1 | 8/2006 | Schwinn et al. |
| 2010/0047775 A1 | 2/2010 | Schwinn et al. |

FOREIGN PATENT DOCUMENTS

| WO | WO 02/06536 | 1/2002 |
| WO | WO 02/38586 | 5/2002 |
| WO | WO 2004/081187 | 9/2004 |
| WO | WO 2006/116197 A2 | 11/2006 |

OTHER PUBLICATIONS

Jacquelin et al, "Allele-dependent transcriptional regulation of human integrin $\alpha_2$ gene", Blood 97(6):1721-1726 (2001).
Kritzik et al, "Nucleotide Polymorphisms in the $\alpha_2$ Gene Define Multiple Alleles That Are Associated With Differences in Platelet $\alpha_2\beta_1$ Density", Blood 92(7):2382-2388 (1998).
Di Paola et al, "Low Platelet $\alpha_2\beta_1$ Levels in Type I von Willebrand Disease Correlate With Impaired Platelet Function in a High Shear Stress System", Blood 93(11):3578-3582 (1999).
Pivalizza, Evan G., "Perioperative Use of the Thrombelastograph® in Patients with Inherited Bleeding Disorders", J. Clin. Anesth. 15:365-370 (2003).
Santoro, Samuel A., "Platelet Surface Collagen Receptor Polymorphisms: Variable Receptor Expression and Thrombotic/Hemorrhagic Risk", Blood 93(11):3575-3577 (1999).
Vincentelli et al, "Acquired von Willebrand Syndrome in Aortic Stenosis", N. Engl. J. Med. 349(4):343-349 (2003).
Kunicki, Thomas J., "The Influence of Platelet Collagen Receptor Polymorphisms in Hemostasis and Thrombotic Disease", Arterioscler. Thromb. Vasc. Biol. 22:14-20 (2002).
Stafford-Smith et al, "Association of Genetic Polymorphisms With Risk of Renal Injury After Coronary Bypass Graft Surgery", American Journal of Kidney Diseases 45(3):519-530 (2005).
Cox et al, "Cytokine Polymorphic Analyses Indicate Ethnic Differences in the Allelic Distribution of Interleukin-2 and Interleukin-1", Transplantation 72(4):720-726 (2001).
Muller-Steinhardt et al, "Cooperative Influence of the Interleukin-6 Promoter Polymorphisms -597, -572 and -174 on Long-Term Kidney Allograft Survival", American Journal of Transplantation 4:402-406 (2004).
Pennesi, E., "A Closer Look at SNPs Suggests Difficulties", Science 281:1787-1789 (1998).
Hacker et al, "Lack of association between an interleukin-1 receptor antagonist gene polymorphism and ulcerative colitis", Gut 40:623-627 (1997).
Pola et al, "Angiotensin-converting enzyme gene polymorphism may influence blood loss in a geriatric population undergoing total hip arthroplasty", Journal of the American Geriatrics Society 50(12):2025-2028 (2002).

(Continued)

*Primary Examiner* — Jehanne Sitton
(74) *Attorney, Agent, or Firm* — Myers Bigel, P.A.

(57) ABSTRACT

The present invention relates, in general, to perioperative bleeding and, in particular, to methods of identifying individuals at risk of perioperative bleeding.

The present invention relates, in general, to perioperative renal dysfunction and, in particular, to methods of identifying individuals at risk of perioperative renal dysfunction.

The present invention relates, in general, to perioperative stroke and, in particular, to methods of identifying individuals at risk of perioperative stroke.

4 Claims, 7 Drawing Sheets

(56) References Cited

OTHER PUBLICATIONS

Shields et al, "The contribution of genetic factors to thrombotic and bleeding outcomes in coronary patients randomized to IIb/IIIa antagonists", Phamacogenomics Journal 2(3):182-190 (2002).
Chew et al, "Preliminary report on the associateion of apolipoprotein E polymorphisms, with postoperative peak serum creatinine concentrations in cardiac surgical patients", Anesthesiology 93(2):325-331 (2000).
Ziegeler et al, Influence of genotype on perioperative risk and outcome, Anesthesiology 99(1):212-219 (2003).
Supplementary European Search Report, European Appln. No. 04800614.2-1222, Date of completion of the search Feb. 14, 2008.
Hegele, Robert A., "SNP Judgments and Freedom of Association", Arteriosclerosis, Thrombosis and Vascular Biology 22:1058-1061 (2002).
Lucentini, Jack, "Gene Association Studies Typically Wrong", The Scientist 24:20 (2004).
Juppner, H., "Functional Properties of the PTH/PTHrP Receptor", Bone 17(2):39S-40S (1995).
International Preliminary Report on Patentability corresponding to International Patent Application No. PCT/US2004/036495 (6 pages) (dated May 8, 2006).
International Search Report and the Written Opinion of the International Searching Authority corresponding to International Patent Application No. PCT/US2004/036495 (11 pages) (mailed Nov. 15, 2005).

METHODS OF IDENTIFYING INDIVIDUALS AT RISK OF PERIOPERATIVE BLEEDING, RENAL DYSFUNCTION OR STROKE

This application is a continuation of U.S. application Ser. No. 13/454,929, filed Apr. 24, 2012, which is a continuation of U.S. application Ser. No. 12/073,113, filed Feb. 29, 2008, now U.S. Pat. No. 8,187,807, which is a continuation of U.S. application Ser. No. 10/979,816, filed Nov. 3, 2004, now U.S. Pat. No. 7,439,019, which claims priority from U.S. Provisional Application No. 60/516,313, filed Nov. 3, 2003, U.S. Provisional Application No. 60/567,793, filed May 5, 2004, and U.S. Provisional Application No. 60/620,666, filed Oct. 22, 2004, the entire contents of these applications being incorporated herein by reference.

TECHNICAL FIELD

The present invention relates, to methods of identifying individuals at risk of perioperative bleeding, perioperative renal dysfunction and/or perioperative stroke.

BACKGROUND

Microvascular bleeding remains a major problem following cardiac surgery with cardiopulmonary bypass (CPB) (Nuttall et al, Anesthesiology 94:773-781, discussion 5A-6A (2001), Hall et al, Cardiovasc. Surg, 10:146-153 (2002)), with up to 5% of patients receiving more than a 10 unit perioperative blood transfusion (Woodman and Harker, Blood 76:1680-1697 (1990)). Approximately 4% of patients require reoperation for hemorrhage (Hall et al, Cardiovasc. Surg. 10:146-153 (2002), Woodman and Harker, Blood 76:1680-1697 (1990)) which is associated with increased mortality and morbidity (Unsworth-White et al, Anannis of Thoracic Surgery 59:664-667 (1995)). Current risk stratification based on clinical, procedural, and biological markers (Wahba et al, Journal of Cardiothoracic & Vascular Anesthesia 11:824-827 (1997), Despotis et al, Anesthesia & Analgesia 82:13-21 (1996)) has been only partially successful, failing to account for much of the postoperative blood loss seen even with "low-risk" primary coronary artery bypass (CABG) surgery (Hardy et al, Canadian Journal of Anaesthesia 38:511-517 (1991)). CPB-induced alterations in the hemostatic system are multifactorial, pertaining to excessive activation of coagulation and fibrinolytic pathways with interplay of cellular and soluble hemostatic and inflammatory systems; hypothermia and hemodilution further complicate the situation (Despotis et al, Annals of Thoracic Surgery 72:S1821-1831 (2001)). Coagulopathy following CPB represents one extreme on a continuum of coagulation function, with perioperative prothrombotic outcomes (e.g. coronary graft thrombosis, myocardial infarction, stroke and pulmonary embolism) at the other end of the spectrum (Spiess and Chandler, Best Practice & Research: Clinical Anaesthesiology 15:195-211 (2001)).

Pathophysiologically, the balance between bleeding, normal hemostasis, and thrombosis is markedly influenced by the rate of thrombin formation and platelet activation (Kunicki and Nugent, Vox Sang. 83 (Suppl 1):85-90 (2002), Slaughter et al, Anesthesiology 80:520-526 (1994)). There is recent evidence that genetic variability modulates the activity in each of these mechanistic pathways (Spiess and Chandler, Best Practice & Research: Clinical Anaesthesiology 15:195-211 (2001)). However, little is known of the role of allotypic coagulation, fibrinolytic and platelet-membrane receptor gene variation in predicting bleeding following CABG surgery; the few studies to date focus only on single-gene variants (Donahue et al, Circulation 107(7): 1003-1008 (2003)). Several prothrombotic genetic polymorphisms are known to exist.

The present invention results, at least in part, from studies designed to investigate the impact of multi-locus genetic influences on the incidence and severity of perioperative bleeding after CABG surgery. The invention provides, in one embodiment, a method of identifying patients with prothrombotic gene polymorphisms, which polymorphisms are associated with increased postoperative bleeding.

Acute renal dysfunction, evidenced by rapid decline in glomerular filtration rate and accumulation of nitrogenous waste products (blood urea nitrogen and creatinine), is a major medical problem occurring in 5% of all patients admitted to the hospital and 30% of those admitted to an intensive care unit (Hou et al, Am. J. Med. 74(2):243-248 (1983)). Furthermore, acute renal injury remains a common, serious complication of cardiac surgery (Conlon et al, Nephrol. Dial Transplant. 14(5):1158-1162 (1999)); multiple etiologies for this observation have been proposed including nephrotoxins, atheroembolism, ischemia-reperfusion, and cardiopulmonary bypass (CPB)-induced activation of inflammatory pathways. Renal failure requiring dialysis occurs in up to 5% of cardiac surgery patients; an additional 8-15% have moderate renal injury (e.g., >1.0 mg/dl peak creatinine rise) (Conlon et al, Nephrol. Dial Transplant. 14(5):1158-1162 (1999), Abel et al, J. Thorac. Cardiovasc. Surg. 71(3):323-333 (1976), Corwin et al, J. Thorac. Cardiovasc. Surg. 98(6)1:1107-1112 (1989), Andersson et al, Thorac. Cardiovasc. 41(4):237-241 (1993), Mora-Mangano et al, Ann. Intern. Med. 128(3):194-203 (1998), Mangos et al, Aust. N Z J. Med. 25(4):284-289 (1995), Ostermann et al, Intensive Care Med. 26(5):565-571 (2000)). Lesser renal injuries are even more common (>50% aortocoronary bypass surgery patients have ≥25% postoperative rise in serum creatinine). In many settings, including cardiac surgery, acute renal failure is independently predictive of the in-hospital mortality rate even after adjustment for comorbidities and other complications (Conlon et al, Nephrol. Dial Transplant. 14(5):1158-1162 (1999), Levy et al, JAMA 275(19):1489-1494 (1996), Chertow et al, Am. J. Med. 104(4):343-348 (1998)); all degrees of renal injury are associated with increased mortality and other adverse outcomes (Stafford-Smith, Chapter 5—In: Newman, ed. 2003 Society of Cardiovascular Anesthesiologists Monograph— Perioperative Organ Protection: Lippincott Williams & Wilkins, pgs. 89-124 (2003)). Unfortunately, typical characteristics (e.g., advanced age, history of atherosclerotic vascular disease) of those presenting for cardiac surgery make them generally a group at high "renal risk" (Conlon et al, Nephrol. Dial Transplant. 14(5):1158-1162 (1999), Greenberg et al, Am. J. Kidney Dis. 29(3):334-344 (1997), Porter, Miner Electrolyte Metab. 20(4):232-243 (1994), Novis et al, Anesth. Analg. 78(1):143-149 (1994)).

Paradoxically, although the kidneys receive more blood flow per gram of tissue than any other major organ, they are also the most vulnerable to ischemic injury. Metabolic demands from active tubular reabsorption and the oxygen diffusion shunt characteristic of renal circulation contribute to the precarious physiology of renal perfusion including low medullary pO2 (10-20 mmHg) (Brezis and Rosen, N. Engl. J. Med. 332(10):647-655 (1995)). Key to regulation of renal blood flow are paracrine systems (e.g., renin-angiotensin system [RAS], nitric oxide[NO]) that modulate microvascular function and oxygen delivery in the renal medulla (Navar et al, Physiol. Rev. 76(2):425-536 (1996)).

The inflammatory response to CPB generates cytokines (e.g., tumor necrosis factor alpha [TNFα], interleukin 6 [IL-6]) both systemically and locally in the kidney (Cunningham et al, J. Immunol. 168(11):5817-5823 (2002), Segerer et al, J. Am. Soc. Nephro. 11(1):152-176 (2000)), that have major effects on the renal microcirculation and may lead to tubular injury (Heyman et al, Exp. Nephrol. 8(4-5):266-274 (2000)). Recent evidence suggests that heritable differences modulate the activation of these pathways.

Although many preoperative predictors have been identified (these are similar to factors predictive of chronic renal dysfunction), risk stratification based on clinical, intraoperative, and biological markers explains only a small part of the variability in postoperative renal dysfunction ((Conlon et al, Nephrol. Dial Transplant. 14(5):1158-1162 (1999), Abel et al, J. Thorac. Cardiovasc. Surg. 71(3):323-333 (1976), Corwin et al, J. Thorac. Cardiovasc. Surg. 98(6)):1107-1112 (1989), Andersson et al, Thorac. Cardiovasc. Surg. 41(4):237-241 (1993), Mora-Mangano et al, Ann. Intern. Med. 128(3):194-203 (1998), Mangos et al, Aust. N Z J. Med. 25(4):284-289 (1995), Ostermann et al, Intensive Care Med. 26(5):565-571 (2000), Novis et al, Anesth. Analg. 78(1):143-149 (1994), Zanardo et al, J. Thorac. Cardiovasc. Surg. 107(6):1489-1495 (1994), Yeh et al, J. Thor. Cardiovasc. Surg. 47:79-95 (1964), Porter et al, J. Thorac Cardiovasc. Surg. 53(1):145-152 (1967), McLeish et al, Surg. Gynecol. Obstet. 145(1):28-32 (1977), Llopart et al, Ren, Fail. 19(2):319-323 (1997), Hilberman et al, J. Thorac. Cardiovasc. Surg. 77(6):880-888 (1979), Heikkinĕn et al, Ann. Chir. Cynaecol. 75(5):203-209 (1985), Gailiunas et al, J. Thorac. Cardiovasc. Surg. 79(2):241-243 (1980), Doberneck et al, J. Thor. Cardiovasc. Surg. 43:441-452 (1962), Bhat et al, Ann. Intern. Med. 84(6):677-682 (1976)). However, little is known regarding the relationship of the several known polymorphisms associated with altered activation of renal paracrine and/or inflammatory pathways, with acute renal injury following aortocoronary bypass graft (CABG) surgery. The few existing studies have focused on only 2 genetic polymorphisms (Apolipoprotein E [ApoE] T448C (ε4), interleukin 6 [IL6] G-174C) (Chew et al, Anesthesiology 93(2):325-331 (2000), Mackensen et al, Ann. Thor. Surg. (in press) (2004), Gaudino et al, J. Thorac. Cardiovasc. Surg. 126(4):1107-1112 (2003)) and do not take into account other important pathways/proteins or interactions between potentially synergistic insults.

The present invention further results, at least in part, from studies designed to investigate the association between genetic variants of inflammatory and paracrine pathways at multiple loci and susceptibility to perioperative acute renal injury.

Despite advances in the field of cardiac surgery, significant neurologic morbidity continues to occur (Wolman et al, Stroke 30(3):514-522 (1999), Roach et al, N. Engl. J. Med. 335(25):185701863 (1996), Newman et al, N. Engl. J. Med. 344:395-402 (2001), Bucerius et al, Ann. Thorac. Surg. 75(2):472-478 (2003)). Indeed, over the past several decades, many technologic advancements in surgery, anesthesia, and the conduct of cardiopulmonary bypass (CPB), coupled with an improved understanding of the pathophysiology of neurologic injury, have allowed surgery to be performed on an increasingly elderly and high-risk group of patients (Ferguson et al, Ann. Thorac. Surg. 73(2):480-489, discussion 9-90 (2002)). Stroke, although less frequent than more subtle types of cerebral injury (such as cognitive dysfunction) (Newman et al, N. Engl. J. Ivied. 344:395-402 (2001)) remains a significant and debilitating complication of cardiac surgery (Roach et al, N. Engl. J. Med. 335(25): 185701863 (1996)). In addition to being a devastating injury to the patient, diminishing quality of life and increasing mortality, stroke following cardiac surgery also incurs a substantial cost in terms of health-care resource utilization (Roach et al, N. Engl. J. Med. 335(25):185701863 (1996)). Despite many years of study to understand factors associated with postoperative stroke, questions exist regarding its pathophysiology, and as a result, the ability to understand who is at risk is far from complete.

The variable incidence of stroke after cardiac surgery is thought to be influenced both by patient and procedural risk factors (Borger et al, Eur. J. Cardiothorac. Surg. 19(5):627-632 (2001)). While many of the procedural risk factors have been incorporated in stroke risk indices from observational studies (Newman et al, Circulation 94(9 Suppl):II74-II80 (1996)), they provide incomplete information regarding the full risks of stroke. These risk-indices and associated factors do not include information regarding the genetic makeup of the patient, raising the possibility that heterogeneity seen in the clinical presentation of stroke (both in incidence and severity) may partly reflect underlying genotype.

The pathophysiology of stroke in non-surgical settings is thought to involve complex interactions between pathways associated with coagulation, inflammation, lipid metabolism, apoptosis, and direct cellular injury. Within each of these broad etiologic pathways, genetic variants have been identified. As a result, identification of specific genetic variants involved in stroke can be thought of in mechanistic terms. Although not exclusively so, it appears that pro-inflammatory and pro-thrombotic genes may play a significant role in the etiology and outcome after stroke in non-operative settings. Recently, polymorphisms involving cyclooxygenase-2 (Cipollone et al, JAMA 291(18):2221-2228 (2004)), apolipoprotein (APOE) (McCarron et al, Stroke 29(9):1882-1887 (1998)), myeloperoxidase (Hoy et al, Atherosclerosis 167(2):223-230 (2003)), interleukin 6 (IL6) (Greisenegger et al, Thromb. Res. 110(4):181-186 (2003), Pola et al, Stroke 34(4):881-885 (2003)), intercellular adhesion molecule-1 (ICAM1) (Pola et al, Stroke 34(4):881-885 (2003)), vascular cell adhesion molecule-1 (VCAM1) (Adams et al, BMC Med. Genet. 4(1):6 (2003)), C-reactive protein (CRP) (Rost et al, Stroke 32(11):2575-2579 (2001), Curb et al, Circulation 107(15):2016-2020 (2003), Ford and Giles, Arterioscler. Thromb. Vasc. Biol. 20(4):1052-1056 (2000)), and various prothrombotic genes (Kahn, Sourth Med. J. 96(4):350-353 (2003), Endler and Mannhalter, Clin., Chim. Acta 330(1-2):31-55 (2003)) have all been examined in studies demonstrating variable relationships to stroke.

The present invention additionally results, at least in part, from studies designed to examine a group of genetic polymorphisms for their potential may influence on perioperative stroke risk (McCarron et al, Stroke 29(9):1882-1887 (1998), Greisenegger et al, Thromb. Res. 110(4):181-186 (2003), Pola et al, Stroke 34(4):881-885 (2003), Rost et al, Stroke 32(10:2575-2579 (2001), Curb et al, Circulation 10705): 2016-2020 (2003), Ford and Giles, Arterioscler. Thromb. Vasc. Biol. 20(4):1052-1056 (2000), Kahn, Sourth Med. J. 96(4):350-353 (2003), Endler and Mannhalter, Clin., Chim Acta 330(1-2):31-55 (2003), Meschia et al, BMC Neurol. 3(1):4 (2003)). These studies have resulted in the identification of specific genetic polymorphisms that modulate the risk of stroke following surgery.

SUMMARY OF THE INVENTION

The present invention relates generally to perioperative bleeding, renal dysfunction and stroke. More specifically, the invention relates to methods of identifying individuals at risk of perioperative bleeding, renal dysfunction and stroke, and to kits suitable for use in such methods.

Objects and advantages of the present invention will the clear from the description that follows.

DETAILED DESCRIPTION OF THE INVENTION

Figure 1:
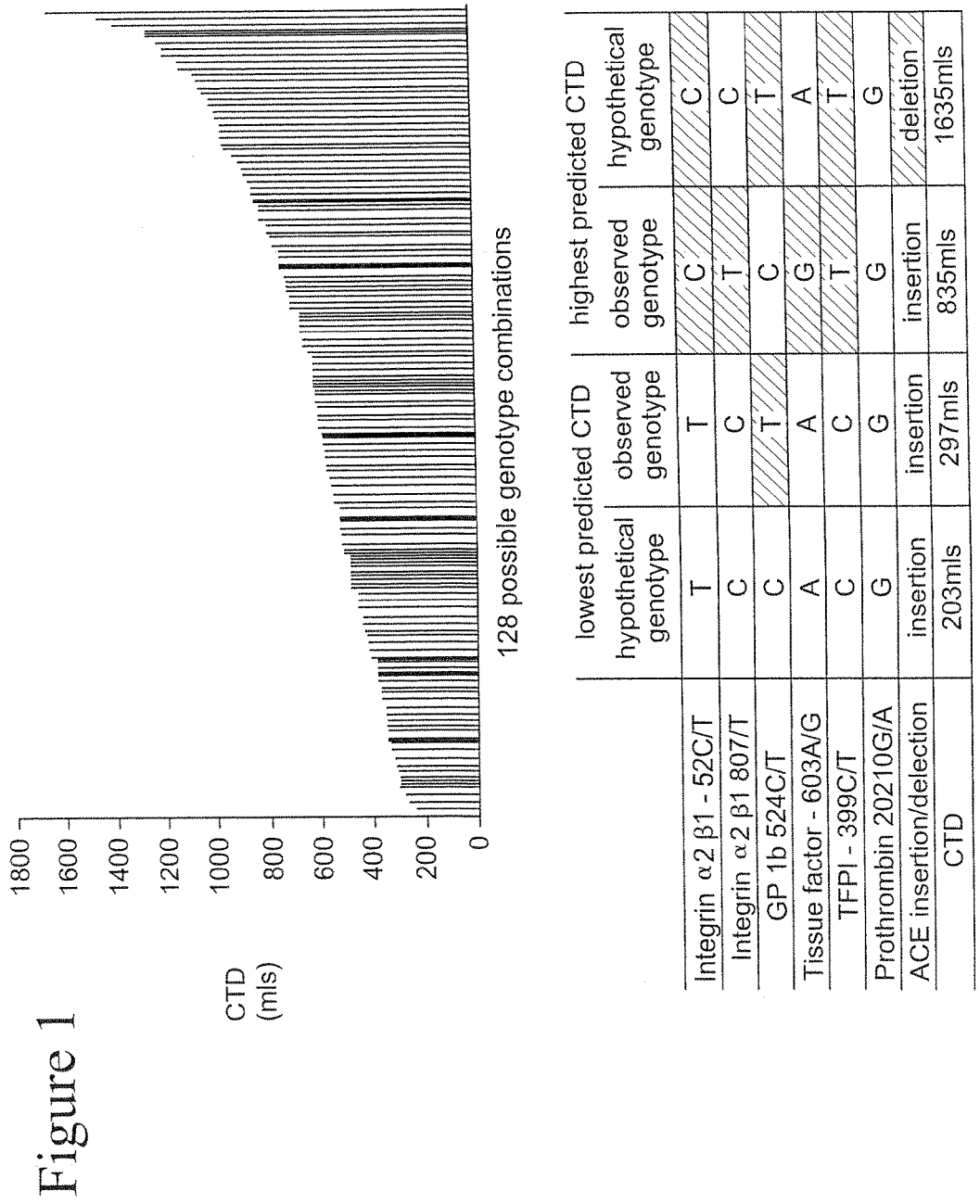
FIG. 1. CTD denotes the predicted chest tube drainage for all the 128 possible allele combinations of the 7 polymorphisms, for the first 12 postoperative hours. Black bars mark allele combinations actually observed in the study population; the gray bars represent hypothetical allele combinations. The shaded cells in the table mark the prothrombotic allele and illustrate clustering of the prothrombotic alleles in the combinations associated with so increased bleeding. The minor prothrombin 20210A allele was rare and did not appear in any of the examples.

In one embodiment, the present invention results from studies designed to prospectively examine specific genetic variants involved in bleeding pathways and how they influence postoperative bleeding. Polymorphisms found to be significantly associated with postoperative bleeding include $\alpha_2\beta_1$ integrin −52C/T and 807C/T dimorphisms, GPIbα 524C/T, tissue factor −603A/G, prothrombin 20210G/A, tissue factor pathway inhibitor −399C/T polymorphisms, and the angiotensin converting enzyme insertion/deletion polymorphism.

Biological effects for each of the single nucleotide polymorphisms (SNPs) referenced above, and described in greater detail in Example 1, have been demonstrated. The present invention provides, in part, definitive association between these genetic variants and clinical postoperative bleeding in the perioperative and intensive care unit setting. This aspect of the invention is exemplified by reference to cardiac surgery patients but includes all perioperative, periprocedure (endoscopy, bronchoscopy, cardiac catheterization, angioplasty, etc.), and intensive care unit settings.

The presence of one or more of the above-referenced polymorphisms present in a sample (e.g., a biological sample such as blood) can be determined using any of a variety of genotyping techniques known in the art. Examples of such techniques include the use of polymerase chain reaction and extension primers (see too Example 1 below). Suitable techniques also include the use of RFLP analysis and mass spectrometry (see also Ye et al, Hum. Mutat. 17(4):305 (2001), Chen et al, Genome Res. 10:549 (2000).)

The genetic variants (SNPs) described above and in Example 1 can be used, for example, to predict postoperative and ICU bleeding. As indicated above, screening for genetic variants of the invention is also relevant for other invasive procedures including but not limited to endoscopy, bronchoscopy, cardiac catheterization, and angioplasty. Preoperative screening for genetic variants enables clinicians to better stratify a given patient for therapeutic intervention, either with drug therapy or with other modalities to alter homeostatic pathways. Additionally, knowledge of genetic variants allows patients to choose, in a more informed way in consultation with their physician, medical versus procedural therapy. Identifying these genetic variants in patients who are already bleeding or having difficulties with coagulation, can result in the alteration or modification of the therapeutic strategy.

As indicated above, preoperative genotype testing can refine risk stratification and improve patient outcome. Based on the genetic risk factors identified, non-specific therapies to reduce thrombin activation and bleeding, such as aprotinin, prostaglandins (Kozek-Langenecker et al, Anesthesia & Analgesia 87:985-988 (1998)) or more aggressive heparin dosing (Despotis et al, Thrombosis & Haemostasis 76:902-908 (1996)), can be employed for at-risk patients. As certain of the prothrombotic alleles that lead to increased bleeding in the immediate postoperative period are later associated with the return of a prothrombotic tendency (Golanski et al, Platelets 12:241-247 (2001)), a biphasic anti-thrombotic therapeutic approach can have merit, initially to halt sub-clinical thrombosis, then postoperatively to prevent thrombotic complications. Optimum timing and dosing of any such intervention can be established by one skilled in the art.

It will be appreciated from a reading of this disclosure that certain of the particular genetic variants are important independently and others interact to become significant in combination with other genes relative to postoperative bleeding.

The invention also relates to kits suitable for use in testing for the presence of the polymorphisms identified above. Such kits can include, for example, reagents (e.g., probes or primers) necessary to identify the presence of one or more of the above-referenced polymorphisms associated with perioperative bleeding.

In another embodiment, the present invention results from studies designed to examine the association between specific genetic variants and perioperative renal dysfunction. When twelve candidate polymorphisms are assessed, two demonstrate strong association with renal injury (>50% decrease renal filtration); these genes include interleukin 6 G572C and angiotensinogen T842C in Caucasians (when present together p<0.0001). Using less stringent criteria for significance (0.01>p>0.001), 4 additional polymorphisms are identified (apolipoproteinE C586T (ε2), angiotensin receptor1 A1166C, and eNOS G894T in Caucasians; eNOS G894T and ACE D/I in African Americans). Adding genetic to clinical predictors resulted in the best model, with overall ability to predict renal injury increasing about 4-fold in Caucasians and doubling in African Americans (p<0.0005). Up to 8 genetic polymorphisms collectively provide a 2-4 fold improvement over clinical factors alone in predicting perioperative renal dysfunction. From a mechanistic perspective, most identified genetic variants are associated with increased renal inflammatory and/or vasoconstrictor responses.

Biological effects for each of the single nucleotide polymorphisms (SNPs) referenced above, and described in greater detail in Example 2, have been demonstrated. This aspect of the invention provides definitive association between these genetic variants and clinical postoperative renal dysfunction in the perioperative and intensive care unit setting. The invention is exemplified by reference to cardiac surgery patients but includes all perioperative, periprocedure (endoscopy, bronchoscopy, cardiac catheterization, angioplasty, etc.), and intensive care unit settings.

The presence of one or more of the above-referenced polymorphisms present in a sample (e.g., a biological sample such as blood) can be determined using any of a variety of genotyping techniques known in the art. Examples of such techniques include the use of polymerase chain reaction and extension primers (see too Example 2). Suitable techniques also include the use of RFLP analysis and mass spectrometry (see also Ye et al, Hum. Mutat. 17(4):305 (2001), Chen et al, Genome Res. 10:549 (2000).)

The genetic variants (SNFs) described above and in Example 2 can be used, for example, to predict postoperative and ICU renal dysfunction.

As indicated above, screening for genetic variants of the invention is also relevant for other invasive procedures including but not limited to endoscopy, bronchoscopy, cardiac catheterization, and angioplasty. Preoperative screening for genetic variants enables clinicians to better stratify a given patient for therapeutic intervention, either with drug therapy or with other modalities. Additionally, knowledge of genetic variants allows patients to choose, in a more informed way in consultation with their physician, medical versus procedural therapy. Identifying these genetic variants in patients who are already experiencing renal injury can result in the alteration or modification of the therapeutic strategy.

As indicated above, preoperative genotype testing can refine risk stratification and improve patient outcome. Based on the genetic risk factors identified, drugs already available and used to delay progression of chronic renal disease (e.g., angiotensin converting enzyme inhibitors and/or angiotensin receptor blockers) may be useful in reducing renal damage in acute settings such as cardiac surgery. Identification of the genetic markers described herein may facilitate individually tailored medical therapy (personalized medicine) designed to reduce acute renal injury and associated morbidity and mortality.

It will be appreciated from a reading of this disclosure that certain of the particular genetic variants are important independently and others interact to become significant in combination with other genes relative to postoperative renal dysfunction.

The invention also relates to kits suitable for use in testing for the presence of the polymorphisms identified above. Such kits can include, for example, reagents (e.g., probes or primers) necessary to identify the presence of one or more of the above-referenced polymorphisms associated with perioperative renal dysfunction.

In yet another embodiment, the present invention results from studies designed to examine the association between specific genetic polymorphisms and stroke risk after surgery (e.g., cardiac surgery). These studies demonstrate that specific genetic variants contribute to the risk of postoperative stroke and suggest that inflammation plays a pivotal role. It will be appreciated from a reading of this disclosure that a SNP pair representing individuals having minor alleles for both of CRP (3'UTR 1846C/T) and IL6 (−174G/C) significantly associated with stroke. Individuals with at least one minor allele at each locus are about three times more likely to have a stroke than individuals without this combination.

Biological effects for the single nucleotide polymorphisms (SNPs) referenced above, and described in greater detail in Example 3, have been demonstrated. The present invention provides definitive association between these genetic variants and clinical postoperative stroke in the perioperative setting. The invention is exemplified by reference to cardiac surgery patients but includes all perioperative, periprocedure (endoscopy, bronchoscopy, cardiac catheterization, angioplasty, etc.), and intensive care unit settings.

The presence of one or more of the above-referenced polymorphisms present in a sample (e.g., a biological sample such as blood) can be determined using any of a variety of genotyping techniques known in the art. Examples of such techniques include the use of polymerase chain reaction and extension primers (see too Example 3). Suitable techniques also include the use of RFLP analysis and mass spectrometry (see also Ye et al, Hum. Mutat. 17(4):305 (2001), Chen et al, Genome Res. 10:549 (2000)).

The genetic variants (SNPs) described above and in Example 3 can be used, for example, to predict postoperative and ICU stroke risk. As indicated above, screening for genetic variants of the invention is also relevant for other invasive procedures including but not limited to endoscopy, bronchoscopy, cardiac catheterization, and angioplasty. Preoperative screening for genetic variants enables clinicians to better stratify a given patient for therapeutic intervention, either with drug therapy or with other modalities. Additionally, knowledge of genetic variants allows patients to choose, in a more informed way in consultation with their physician, medical versus procedural therapy. Identifying these genetic variants in patients who decide to undergo surgery or other invasive procedure enables health care providers to design altered therapeutic strategies aimed at preventing the incidence of stroke in the subset of patients with enhanced risk. In addition, identifying these genetic variants in patients who have already experienced a stroke might also lead to alteration or modification in the therapeutic strategy.

As indicated above, preoperative genotype testing can refine risk stratification and improve patient outcome. Based on the genetic risk factors identified, drugs already available and used to minimize the risk of stroke and/or damage associated therewith (e.g., Apoprotinin) can be useful in reducing stroke risk/damage in acute settings, for example, cardiac surgery. Identification of the genetic markers described herein can facilitate individually tailored medical therapy (personalized medicine) designed to reduce stroke risk and associated morbidity and mortality. Perioperative screening can facilitate alterations in the usual course of the surgical procedure with institution of procedures designed to additionally reduce this risk (e.g., cardiac surgery without aortic cross-clamping).

The invention also relates to kits suitable for use in testing for the presence of the polymorphisms identified above. Such kits can include, for example, reagents (e.g., probes or primers) necessary to identify the presence of one or more of the above-referenced polymorphisms associated with perioperative stroke.

In a further embodiment, the present invention relates to methods of identifying compounds suitable for use in minimizing the risk of stroke.

These methods can comprise screening compounds for their ability to modulate (e.g., inhibit) inflammation (e.g., perioperative inflammation). Such methods are made possible by the presently described interaction of two specific pathways.

Certain aspects of the invention can be described in greater detail in the non-limiting Examples that follow.

EXAMPLE 1

Experimental Details
Study Design

The PeriOperative Genetics and Outcomes (POGO) study is an ongoing prospective and longitudinal study, including over 3300 consenting patients scheduled for cardiac surgery.
Data Collection and Management Data was prospectively collected as part of a quality assurance database, including demographic, historical, clinical, laboratory, and investigational test information, resource utilization, and adverse outcome. All outcomes are prespecified and defined by protocol.
Study Sample All patients qualifying within the enrollment period were entered. Of the 3300 patients enrolled, 740 were analyzed for the bleeding clinical end point. During a prospectively identified time period, data pertaining to postoperative bleeding was collected from enrolled patients undergoing primary elective CABG surgery. The following exclusion criteria were used: presence of liver disease, end stage renal disease, preexisting coauulopathy, emergency procedure (including administration of thrombolytic drugs within 48 hours), and reoperation for bleeding.
Patient Data Collection and Definition of Phenotypes:

Blood was collected prior to anesthetic induction for isolation of genomic DNA. Co-variate data included age, sex, race, height, weight, smoking, diabetes, preoperative hemoglobin level and platelet count, preoperative aspirin or intravenous heparin therapy, duration of cardiopulmonary bypass and number of bypass grafts performed, heparin dose, protamine dose, intraoperative blood product usage. Cardiopulmonary bypass was conducted using mild to moderate hypothermia and a target activated clotting time of 480 seconds, with a crystalloid primed circuit and cold blood/crystalloid cardioplegia. All patients received intraoperative ε-aminocaproic acid infusions to inhibit excessive fibrinolysis and protamine sulphate to reverse heparin anticoagulation. The outcome variable was defined as 12 hour postoperative chest tube drainage (CTD).

After collection, genetic samples were linked to covariate and phenotypic variables in a relational database with extensive quality control features; databases were deidentified to ensure patient confidentiality.

Rationale for Candidate Polymorphism Selection:

Overall, 78 candidate genes representing one of nine mechanistic pathways involved in the pathophysiology of organ dysfunction after CPB were selected after a comprehensive review of expression studies, linkage data, functional and positional guesses, and population-based association studies reported in the literature. Broadly, these polymorphisms are grouped into genes involved in inflammatory, thrombosis/coagulation, vascular tone, vascular growth, renin-angiotensin axis, cell-matrix adhesion, reperfusion, lipid and homocysteine metabolism, and cellular homeostasis. Of the 160 candidate polymorphisms identified from public databases, 19 were selected for their high likelihood of association with bleeding outcomes (Table 2). Selection strategies included polymorphisms with previously demonstrated high likelihood (based on location and type) of functionally significant effects on the gene product itself (nonsense or misssense non-synonymous variants or frame shift insertions/deletions in the coding sequence), or in the response of the gene to the product of other genes (i.e., transcription factors) through mutations in the promoter or control sequence of a gene (Tabor et al, Nat. Rev. Genet. 3:391-397 (2002)).
Structure Gene Polymorphism Selection:

58 unlinked marker gene polymorphisms were chosen to assess/control for population admixture (genomic control).
Isolation of Genomic DNA and Genotype Analysis:

DNA extraction was performed using the Puregene™ system (Gentra Systems, Minneapolis, Minn.), quantitated and stored at 4° C. under chloroform. The genotyping assays were conducted at Agencourt Bioscience Corporation (Beverly, Mass.) by Matrix Assisted Laser Desorption/Ionization, Time-Of-Flight (MALDI-TOF) mass spectrometry, using the Sequenom™ MassARRAY™ system (Sequenom, San Diego, Calif.) (Sun et al, Nucleic Acids Research 28:E68 (2000)). Polymerase chain reaction and extension primers for each polymorphism are presented in Tables 5 and 6 along with the details of the polymorphisms. The genotyping accuracy of the Sequenom™ MassARRAY™ system was estimated at 99.6% (Gabriel et al, Science 296:2225-2229 (2002)). Polymorphisms with error rates>2%, with genotype call rates<75%, or departing from Hardy-Weinberg equilibrium ($p<0.01$) were regenotyped. Reproducibility of genotyping was validated by scoring a panel of 6 polymorphisms in 100 randomly selected patients using direct sequencing on an ABI3700 capillary sequencer (Applied Biosystems, Foster City, Calif.).

Angiotensin converting enzyme (ACE) deletion and insertion alleles were identified on the basis of polymerase chain reaction amplification of the respective fragments from the intron 16 of the ACE gene, size fractionation and electrophoretic visualization, as described (Lindpaintner et al, N. Engl. J. Med. 332:706-711 (1995)). The results were scored by two independent investigators, blinded to the clinical phenotype.
Statistical Analysis Descriptive statistics were calculated for all 19 candidate polymorphisms, including allele frequencies, Hardy-Weinberg equilibrium and linkage disequilibrium, for the overall study population as well as for gender and race subgroups.

Prior to analysis, the three-level genotypes were collapsed into two-level genotypes based on the absence or presence of the putative deleterious allele. This was done primarily for sample size reasons as the frequency of minor alleles did not allow consideration of all genotypes individually.

Individual linear regression models were constructed to test the hypothesis that the absence or presence of an allele, either singly or in combination with other alleles, was associated with postoperative bleeding. Each polymorphism was considered as a main effect, and was also paired with each of the other polymorphisms to investigate all possible two-way interactions.

The next stage of analysis was to develop a multiple linear regression model, predicting 12 hour chest tube drainage, with all 19 selected candidate gene polymorphisms, and all the significant interaction terms as identified above. Terms which became non-significant in this multivariable model were removed from the model until only significant terms remained. Seven different polymorphisms were represented in the final model. The resulting combination of individual allelic effects and interaction terms constitute the final genetic model (Table 3). Predicted CTD values for all 128 ($2^7$) possible genotypes were generated by this model (FIG. 1).

A second predictive model was developed using clinical, operative, and demographic variables to predict CTD (the "clinical" model). Finally, all of the predictors from the genetic and clinical models were combined into one model, to address the question of whether genetic information would add predictive ability to the clinical model.

Potential bias from population admixture was investigated in the following ways. First, self-reported race (African American or Caucasian; no other race was sufficiently represented) was tested directly as a predictor of CTD. Secondly, each polymorphism was tested individually in interaction with race as a predictor of CTD. Finally, after the development of the final combined genetic and clinical model, race was included as a covariate in the multivariable model and tested again.

All statistical analysis was performed using SAS/Genetics system version 8.02 (SAS Inc, Cary, N.C.). Continuous variables will be described as mean+/−standard deviation, categorical variables will be described as percentages.

Results

Total enrollment in the perioperative genomic project was 3300. The final size of the sample for this endpoint was 740.

Self-reported black or white race was not associated with bleeding either as an independent predictor or as an interaction term with any of the candidate polymorphisms. A similar analysis using structure genes to assess population admixture also did not correlate with postoperative bleeding. Therefore, the sample was assessed as a single population for all further analyses. Characteristics of the 19 prospectively identified candidate polymorphisms studied are defined for this population in Table 1. Prothrombotic physiology is associated with minor alleles except for $\alpha_2\beta_1$ integrin −52C/T and ACE intron 16 del/ins polymorphisms, where the wild-type major alleles are prothrombotic. Of clinical relevance, many prothrombotic minor alleles are relatively common in the study population (frequency>0.1; see Table 1), however, a significant subgroup are present at lower frequency (0.02-0.09). Study population demographics and clinical co-variates considered related to postoperative bleeding are detailed in Table 2.

Seven polymorphisms demonstrate significant associations with postoperative bleeding, either independently or in interaction with each other (Table 3). These included the $\beta_2\beta_1$ integrin −52C/T and 807C/T dimorphisms, GPIb$\alpha$ 524C/T, tissue factor −603A/G, prothrombin 20210G/A, tissue factor pathway inhibitor −399C/T and ACE intron 16 del/ins polymorphisms. FIG. 1 models the predicted chest tube drainage for all possible genotype combinations of the seven polymorphisms listed in Table 3, depicting the observed and hypothetical genotype combinations associated with the highest and lowest values of chest tube drainage. This Figure illustrates the major effect that a combination of multi-locus, genetic polymorphisms may have on the variability in bleeding seen after primary CABG surgery.

Genetic factors predict bleeding. The final genetic multivariate linear regression model including these seven polymorphisms had an $R^2$ value of 0.09, predicting 9% of the variability in CTD. Remarkably, this was more predictive than the model encompassing both preoperative co-morbidities and intraoperative risk factors (Table 3). Combining these clinical and genetic predictors produced a powerful model, predicting 14% of CTD variability ($R^2$ value of 0.14). This indicates that genetic effects are primarily independent of, and carry more predictive power than, clinical effects in the study. Combining the genetic and clinical factors improves prediction of postoperative bleeding.

Surprisingly, three of the four two-way genetic interactions identified in the multivariable model identify less bleeding with wild type genotypes than with any combination of the pro-thrombotic alleles. The remaining genetic interaction shows a similar pattern but one prothrombotic allele combination is associated with less bleeding than the wild type group. In other words, in general, prothrombotic polymorphisms appear to be associated with more rather than less bleeding after coronary bypass surgery.

Linkage disequilibrium was present between some of the candidate polymorphisms (Table 4). Confirmation was provided of previously noted within-gene linkage disequilibrium between the $\beta_2\beta_1$ integrin −52C/T and 807C/T dimorphisms (Jacquelin et al, Blood 97:1721-1726 (2001)) and the two tissue factor polymorphisms (Arnaud et al, Arteriosclerosis, Thrombosis & Vascular Biology 20:892-898 (2000)). In addition linkage disequilibrium between the $\alpha_2\beta_1$ integrin 807C/T and the GPIb$\alpha$ 524C/T polymorphisms was demonstrated.

Conclusions

The findings of the study strongly confirm a genetic basis for bleeding after coronary bypass surgery. In an analysis of nineteen prothrombotic gene polymorphisms, seven alleles were identified that, in interaction with each other, result in a two fold increase in the ability to predict bleeding, compared to models including only clinical factors. Curiously, a pattern emerged with prothrombotic polymorphisms being generally associated with more rather than less bleeding, reflected by 12 hour postoperative chest tube drainage. This study is the first to demonstrate the complex interaction of multiple genetic and clinical factors impacting bleeding after the hemostatic challenge of cardiopulmonary bypass. In addition, a role of several previously known bleeding risk factors was confirmed (Table 3).

While bleeding after cardiac surgery is well described as a major risk factor for adverse outcome, very little is known regarding the genetic basis of this serious problem. In a study of 517 patients undergoing various cardiac surgical procedures (Donahue at al, Circulation 107(7):1003-1008 (2003)), Donahue and colleagues identified an association between reduced bleeding at 12 and 24 hours after surgery and the Factor V Leiden polymorphism; there were 26 heterozygotes for the prothrombotic allele in the study group. However, in the current study it was not possible to confirm such an association even when gene interactions were taken into account. Also conflicting with the general pattern of observations of this study was the reduction of bleeding with a prothrombotic polymorphism noted by Donahue at al. Variability in repeating results has previously been noted for alleles occurring with low frequency (Croft at al, Thrombosis & Haemostasis 81:861-864 (1999)) such as Factor V Leiden. This may be explained by differing study conditions, including selection of antifibrinolytic agent (all patients in the current study received a lysine analogue agent, whereas many in the Donahue study received the serine protease inhibitor aprotinin), and heterogeneity of surgery type in the Donahue study. Alternately, effects such as linkage disequilibrium and population admixture may contribute to differences in findings between studies. The approach used in this study, of choosing to examine multiple genes and their interactions in the context of other clinical factors, is rapidly becoming state of the art, in the context of reports of gene-gene and gene-environment interactions related to outcome (Croft et al, Circulation 104:1459-1463 (2001), Visanji et al, British Journal of Haematology 110:135-138 (2000)), rather than single gene association studies.

The present findings indicate that alleles previously associated with risk of thrombosis are associated with more bleeding after cardiac surgery. Although seemingly reversed from expected associations, this is consistent with previous findings that platelet activation and thrombin generation during CPB are associated with more postoperative bleeding (De Somer et al, Journal of Thoracic & Cardiovascular Surgery 123:951-958 (2002), Despotis et al, Thrombosis & Haemostasis 76:902-908 (1996)). While collagen and thrombin display a synergistic effect promoting activation and degranulation of platelets, platelet activation during CPB increases both markers of thrombin generation and bleeding after cardiac surgery (Kozek-Langenecker et al, Anesthesia & Analgesia 87:985-988 (1998)). Therefore, increased consumption of activated, thrombotic elements may be modulated by the polymorphisms described, and contribute to more bleeding in this setting.

The functional effects of the alleles evaluated in this study include modulation of platelet activation and thrombin generation. This may alter responses to surgically exposed collagen and tissue factor, which are known to affect postoperative bleeding (De Somer et al, Journal of Thoracic & Cardiovascular Surgery 123:951-958 (2002), Despotis et al, Thrombosis & Haemostasis 76:902-908 (1996), Kozek-Langenecker et al, Anesthesia & Analgesia 87:985-988 (1998), Boisclair et al, Blood 82:3350-3357 (1993), Chung et al, Circulation 93:2014-2018 (1996)). The 807C and −52T minor alleles in the $\alpha_2$ gene of the $\beta_2\beta_1$ integrin, downregulate the surface expression of this primary collagen receptor (Jacquelin et al, Blood 97:1721-1726 (2001)), Kunicki et al, Blood 89:1939-1943 (1997)), reducing platelet affinity for collagen and prothrombotic outcomes (Kunicki, Arteriosclerosis, Thrombosis & Vascular Biology 22:14-20 (2002), Santoso et al, Blood 93:2449-2453 (1999)). Similarly, the 524C allele of GPIbα, the platelet adhesion receptor binding to exposed collagen via von Willebrand factor, is associated with fewer coronary thromboses than the 524T allele, potentially by modifying the structure and function of the GPIbα chain (Kunicki, Arteriosclerosis, Thrombosis & Vascular Biology 22:14-20 (2002)). These alleles were found to be associated with less bleeding after cardiac surgery than the prothrombotic alleles. A similar effect was seen with the −603A tissue factor allele, associated with reduced plasma tissue factor levels (Moatti et al, Thrombosis & Haemostasis 84:244-249 (2000), Arnaud et al, Arteriosclerosis, Thrombosis & Vascular Biology 20:892-898 (2000)), the −33C tissue factor pathway inhibitor allele, associated with higher plasma levels of tissue factor pathway inhibitor, (Moatti et al, Thrombosis & Haemostasis 84:244-249 (2000) and the insertion allele of the ACE polymorphism, known to reduce the risk of venous thrombosis (Philipp et al, Thrombosis & Haemostasis 80:869-873 (1998)). The prevailing pattern is that prothrombotic alleles are associated with increased bleeding, probably by promoting consumptive platelet activation and thrombin generation during cardiopulmonary bypass.

Genetic association studies have limitations. Many prothrombotic polymorphisms that broadly involve the same effect in the same physiologic pathway were studied—while some alleles decrease function and others increase, they all affect thrombosis in a similar way. By the nature of examining numerous multi-locus interactions, multiple comparisons are necessary, and prospective studies, including mechanistic aspects, will be required to confirm the present results. However, although analysis of gene-gene interactions does increase the number of tests performed, these findings are remarkably consistent involving similar directional effects on thrombotic and platelet activation pathways; the consistency of the observations provides confidence that the findings are rooted in biology and not spurious testing. There may be other important alleles, not identified as candidate polymorphisms or in linkage disequilibrium with studied polymorphisms (Jorde, Genome Research 10:1435-1444 (2000)), that have been overlooked in the present study. While population admixture is a potential confounder (Deng, Genetics 159:1319-1323 (2001)), evidence of any population stratification affecting this endpoint was not found, either with self-declared race or a more in depth genetic population stratification evaluation.

TABLE 1

| Gene product | Polymorphism* | Prothrombotic allele | Phenotype | Minor allele frequency White (n=) | Minor allele frequency Black (n=) |
| --- | --- | --- | --- | --- | --- |
| Platelet Membrane Glycoproteins | −52C/T | −52C[1,2] | ↑ surface receptor expression | 0.33 | 0.4 |
| Platelet glycoprotein IaIIa ($\alpha_2\beta 1$ integrin) | 807C/T | 807T[2] | ↑ surface receptor expression and collagen binding | 0.38 | 0.3 |
| Platelet glycoprotein Ibα (GPIbα) | −5T/C | −5C[2] | ↑ surface receptor expression | 0.13 | 0.21 |
| | 524C/T (Thr145Met) | Met145 (Ko$^a$)[2] | unknown | 0.09 | 0.19 |

TABLE 1-continued

| Gene product | Polymorphism* | Prothrombotic allele | Phenotype | Minor allele frequency White (n=) | Minor allele frequency Black (n=) |
|---|---|---|---|---|---|
| Platelet glycoprotein IIIa ($\beta_3$ integrin) | 1565T/C (Leu33Pro) | Pro33 (Pl$^{A2}$)[3] | ↑ sensitivity to activation | 0.15 | 0.11 |
| Platelet glycoprotein VI (GPVI) | 13254T/C (Ser219Pro) | Pro219[4] | unknown | 0.15 | 0.23 |
| Coagulation Factors | | | | | |
| Tissue factor (TF) | −1208del/ins | −1208ins[5] | ↑ level | 0.54 | 0.46 |
| | −603A/G | −603G[5] | ↑ level | 0.49 | 0.57 |
| Tissue factor pathway inhibitor (TFPI) | −399C/T | −399T[6] | ↓ level | 0.89 | 0.11 |
| | 1006G/A (Val264Met) | Met264[7] | ↓ level | 0.02 | 0.01 |
| Prothrombin | 20210G/A | 20210A[8] | ↑ level | 0.02 | 0.01 |
| Coagulation factor V | 1691G/A (Arg506Gln) | Gln506 (FV Leiden)[9,10] | APCR | 0.02 | 0.003 |
| | −854(G/A | −854A[11,12] | ↑ level | 0.14 | 0.11 |
| Fibrinogen-β chain (FGB) | −455G/A | −854[11,12] | ↑ level | 0.17 | 0.08 |
| | −148C/T | −148T[11,12] | ↑ level | 0.17 | 0.12 |
| Fibrinolytic Factors | | | | | |
| Plasminogen activator inhibitor type 1 (PAI-1) | −675ins/del (5G/4G) | −675del (4G)[13] | ↑ level | 0.54 | 0.38 |
| Other Prothrombotic Factors | | | | | |
| Thrombomodulin (THBD) | 1959C/T (Ala455Val) | Val455[13,14] | unknown | 0.19 | 0.1 |
| Methylenetetrahydrofolate reductase (MTHFR) | 677C/T (Ala222Val) | Val222[15] | ↓ enzyme activity, ↑homocysteine level | 0.32 | 0.19 |
| Angiotensin converting enzyme (ACE) | Intron 16 del/ins | Intron 16 del[16,17] | ↑ enzyme activity | 0.46 | 0.38 |

Table 1. Candidate polymorphisms assessed
*Minus signs indicate the number of nucleotides upstream to the transcription-initiation site. Major (wild-type) alleles are indicated to the left. For coding region polymorphisms, the resulting nonsynonymous amino acid substitution in shown in parentheses. APCR-activated protein C resistance.
[1]Jacquelin et al, Blood 97: 1721-1726 (2001)
[2]Kunicki et al, Arteriosclerosis, Thrombosis & Vascular Biology 22: 14-20 (2002)
[3]Feng et al, Arteriosclerosis Thrombosis & Vascular Biology 19: 1142-1147 (1999)
[4]Croft et al, Circulation 104: 1459-1463 (2001)
[5]Arnaud et al, Arteriosclerosis, Thrombosis & Vascular Biology 20: 892-898 (2000)
[6]Moatti et al, Thrombosis & Haemostasis 84: 244-249 (2000)
[7]Moatti et al, Arteriosclerosis, Thrombosis & Vascular Biology 19: 862-869 (1999)
[8]Girolami et al, Blood Reviews 13: 205-210 (1999)
[9]Donahue et al, Circulation 107(7): 1003-1008 (2003)
[10]Rosendaal et al, Blood 85: 1504-1508 (1995)
[11]Green, Annals of the New York Academy of Sciences 936: 549-559 (2001)
[12]Cook et al, American Journal of Epidemiology 153: 799-806 (2001)
[13]Eriksson et al, Proceeding s of the National Academy of Sciences of the United States of America 92: 1851-1855 (1995)
[14]Wu et al, Circulation 103: 1386-1389 (2001)
[15]Arruda et al, Thrombosis & Haemostasis 77: 818-821 (1997)
[16]Philipp et al, Thrombosis & Haemostasis 80: 869-873 (1998)
[17]Hooper et al, American Journal of Hematology 70: 1-8 (2002)

TABLE 2

| Demographics | |
|---|---|
| Age (years) | 63 (+/−11) |
| Race (% Caucasian) | 80* |
| Height (cm) | 171 (+/−14) |
| Weight (Kg) | 86 (+/−19) |
| Co-morbidities | |
| Diabetes (%) | 35 |
| Hypertension (%) | 72 |
| Current smokers (%) | 31 |
| Previous myocardial infarction (%) | 26 |
| Congestive cardiac failure (%) | 16 |
| Previous stroke (%) | 6 |
| Clinical co-variates related to bleeding | |
| Preoperative aspirin use (%) | 83 |
| Preoperative heparin infusion (%) | 42 |
| Preoperative platelet count (×10$^6$/ml) | 213 (+/−68) |
| Preoperative hemoglobin (g/dl) | 13.3 (+/−1.7) |
| Intraoperative factors | |
| Number of bypass grafts | 3.3 (+/−0.8) |
| Cardiopulmonary bypass duration (minutes) | 108 (+/−42) |
| Total heparin dose (units) | 39000 (+/−16000) |
| Total protamine dose (mg) | 290 (+/−100) |
| Packed red blood cells transfused (units) | 1.2 (+/−1.4) |
| Fresh frozen plasma transfused (ml) | 75 (+/−260) |
| Platelets transfused (ml) | 47 (+/−134) |

Table 2. Characteristics of the study population
*15% of our population were African-American; the remaining 5% were self-reported as Hispanic, Native American or Asian.

TABLE 3

| Individual polymorphisms | Genetic model F value | P value | Combined model F value | P value |
|---|---|---|---|---|
| $\alpha_2\beta_1$ integrin −52C/T | 7.6 | 0.01* | 6.3 | 0.01* |
| $\alpha_2\beta_1$ integrin 807C/T | 1.4 | 0.24 | 1.7 | 0.19 |
| GPIbα 524C/T | 7.5 | 0.01* | 8.8 | <0.01* |
| Tissue Factor −603A/G | 0.0 | 0.94 | 0.13 | 0.72 |
| Prothrombin 20210G/A | 0.0 | 0.98 | 0.11 | 0.74 |
| TFPI −399C/T | 6.5 | 0.01* | 5.9 | 0.02* |
| ACE insertion/deletion | 6.8 | 0.01* | 6.1 | 0.01* |
| 2-way interactions | | | | |
| $\alpha_2\beta_1$ −52C/T and $\alpha_2\beta_1$ 807C/T | 12.3 | <0.01* | 7 | <0.01* |
| $\alpha_2\beta_1$ −52C/T and tissue factor −603A/G | 6.6 | 0.01* | 6.4 | 0.01* |
| GPIbα 524C/T and tissue factor −603A/G | 4.2 | 0.04* | 3.7 | 0.06 |
| Prothrombin 20210G/A and TFPI −399C/T | 5.0 | 0.03* | 4.8 | 0.03* |

| Clinical Co-variates | Clinical model F value | P value | | |
|---|---|---|---|---|
| Age | 5.8 | 0.02* | 1.8 | 0.18 |
| Weight | 7.9 | <0.01* | 2.1 | 0.14 |
| Height | 11.4 | <0.01* | 6 | 0.01* |
| Diabetes | 6.8 | <0.01* | 1 | 0.33 |
| Preoperative hemoglobin level | 10.9 | <0.01* | 3.9 | 0.05 |
| Preoperative platelet count | 3.8 | 0.05* | 2.5 | 0.12 |
| Cardiopulmonary bypass duration | 4.5 | <0.01* | 3.6 | 0.06 |

Table 3 Results of three multivariate linear regression models testing the association of polymorphisms and clinical co-variates with chest tube drainage. The minor allele is tested as absent or present (heterozygote or homozygote). The $R^2$ values for the clinical, genetics and combined models are 0.07, 0.09 and 0.14 respectively. A statistically significant p value <0.05 is denoted by *.

TABLE 4

| Polymorphism | $\alpha_2\beta_1$ -52C/T | $\alpha_2\beta_1$ 807C/T | GPIbα 524C/T | GPIbα -5T/C | TF -603A/G | TFdel/ins | THBD 1959C/T | ACE del/ins |
|---|---|---|---|---|---|---|---|---|
| $\alpha_2\beta_1$ -52C/T | X | ■ | ▨ | | | | | |
| $\alpha_2\beta_1$ 807C/T | ■ | X | | | | | | |
| GPIbα 524C/T | ▨ | ■ | X | ■ | | | ■ | |
| GPIbα -5T/C | | | ■ | X | | | | |
| TF -603A/G | | | | | X | ■ | | ▨ |
| TFdel/ins | | | | | ■ | X | | |
| THBD1959C/T | | | ■ | | | | X | |
| ACEdel/ins | | | | | ▨ | | | X |

Pair-wise linkage disequilibrium (LD) between candidate polymorphisms. Multiple comparisons were performed, thus possible LD was defined as a p-value of 0.01-0.05 (grey squares) and likely LD by a disequilibrium p-value of 0-0.01 (black squares).

TABLE 5

| Gene Name | Gene Symbol[1] | Gene Map Locus | Gene Region | Poly-morphism | Aminoacid Substitution | dbSNP ID[2] | Intermediate Phenotype | Previous Association Studies |
|---|---|---|---|---|---|---|---|---|
| I. Platelet Membrane Glycoproteins | | | | | | | | |
| Integrin, alpha 2 (alpha 2 subunit of VLA-2 receptor, platelet GPIaIIa, CD49B) | ITGA2 | 5p11.12 | 5'-UTR | −52C/T | — | rs28095 | −52C = ↑surface $\alpha_2\square$, receptor expression; altered affinity for Sp1/Sp3 transcription factors | |
| | | | exon 7 | 807C/T | F253F | rs1800198 | 807T☐↑surface $\alpha_2\beta_1$ receptor expression; ↑typeI collagen binding | MI, post-CABG MI, stroke |
| Platelet glycoprotein Ib, alpha polypeptide (GPIbα) | GP1BA | 17pter-p12 | 5'-UTR | −5 T/C | — | rs2243093 | −5C = ↑surface receptor expression (Kozak dimorphism) | MI |
| | | | exon 2 | 524C/T | T145M (Ko$^b$/Ko$^a$) | rs6065 | unknown | |
| Integrin, beta 3 (platelet GPIIIa, CD61) | ITGB3 | 17q21.32 | exon 3 | 1565T/C | L33P (Pl$^{A1}$/Pl$^{A2}$) | rs5918 | Pl$^{A2}$ = ↑sensitivity to activation; ↑platelet aggregability; ☐fibrinogen binding | early CAD/MI |
| Platelet glycoprotein VI (GPVI) | GP6 | 19q13.4 | exon 5 | 13254T/C | S219P | rs1613662 | unknown | MI |
| II. Coagulation Factors | | | | | | | | |
| Coagulation factor III (Thromboplastin, Tissue factor) | F3 | 1p22-p21 | 5'-UTR | −1208del/ins | — | — | −1208ins = ↑TF level | early CAD/MI, early first CABG, venous thromboembolic disease |
| | | | 5'-UTR | −603A/G | — | rs1361600 | −603G = ↑TF level | |

TABLE 5-continued

| Gene Name | Gene Symbol[1] | Gene Map Locus | Gene Region | Polymorphism | Aminoacid Substitution | dbSNP ID[2] | Intermediate Phenotype | Previous Association Studies |
|---|---|---|---|---|---|---|---|---|
| Tissue factor pathway inhibitor (lipoprotein-associated coagulation inhibitor) | TFPI | 2q31-q32.1 | 5'-UTR | −399C/T | — | — | −399T = ☐total and post-heparin TFPI level | |
| | | | exon 9 | 1006G/A | V264M | rs5940 | M264 = ☐total and free TFPI level | acute coronary syndromes |
| Coagulation factor II (Prothrombin) | F2 | 11p11-q12 | 3'-UTR | 20210G/A | — | rs1799963 | 20210A☐↑prothrombin level | |
| Coagulation factor V (proaccelerin, labile factor) | F5 | 1q23 | exon 10 | 1691G/A | R506Q (Factor V Leiden) | rs6025 | Q506 (FV Leiden) = APCR | deep us thrombosis, MI, stroke |
| Fibrinogen, B beta polypeptide | FGB | 4q28 | 5'-UTR | −854G/A | — | rs1800791 | −854A = ↑FGB level; ↑basal transcription rate | |
| | | | 5'-UTR | −455G/A | — | rs1800790 | −455A = ↑FGB level; ↑basal transcription rate | |
| | | | 5'-UTR | −148C/T | — | rs1800787 | −148T = ↑FGB level | |
| III. Fibrinolytic Factors | | | | | | | | |
| Serine (or cysteine) proteinase inhibitor, clade E (nexin, plasminogen activator inhibitor type 1, PAI-1), member 1 | SERPINE1 | 7q21.3-q22 | 5'-UTR | −675ins/del (5G/4G) | — | rs1799768 | −675del (4G) = ↑PAI-1 level | early CAD/MI, atherosclerosis |
| IV. Other Prothrombotic Factors | | | | | | | | |
| Thrombomodulin | THBD | 20p11.2 | exon 1 | 1959C/T | A455V | rs1042579 | unknown | V455 = CAD/MI |
| 5,10-Methylenetetrahydrofolate reductase | MTHFR | 1p36.3-p36.2 | exon 4 | 677C/T | A222V | rs1801133 | V222 = ☐enzyme activity (thermolabile); ↑homocysteine level | early CAD |
| Angiotensin I converting enzyme (peptidyl-dipeptidase A) 1 | ACE | 17q23 | intron 16 | in16del/ins | — | — | in16 del = ↑enzyme activity | early CAD/MI |

Candidate genes and polymorphisms studied: intermediate functional phenotypes and associations to thrombotic outcomes
NOTES:
[1]gene symbols are taken from OMIM (catalog of human genes and genetic disorders)
[2]from NCBI's dbSNP public database
UTR —untranslated region

TABLE 6

| Gene Symbol[1] | Polymorphism | dbSNP ID[2] | PCR Primers | Extension Primer |
|---|---|---|---|---|
| ITGA2 | −52C/T | rs28095 | | |
| | 807C/T | rs1800198 | ACGTTGGATGTGGCCTATTAGCACCAAAAC<br>ACGTTGGATGAGACATCCCAATATGGTGGG | TTACCTTGCATATTGAATTGCTCC |
| GP1BA | −5T/C | rs2243093 | ACGTTGGATGATCCACTCAAGGCTCCCTTG<br>ACGTTGGATGTTGGCAGCAGGAGCAGCAAG | GGCTCCCTTGCCCACAGG |
| | 524C/T | rs6065 | ACGTTGGATGTGTTGTTAGCAGACTGAGC<br>ACGTTGGATGAAGGCAATGAGCTGAAGACC | TCCAGCTTGGGTGTGGGC |
| ITGB3 | 1565T/C | rs5918 | ACGTTGGATGCCTTCAGCAGATTCTCCTTC<br>ACGTTGGATGTTGCTGGACTTCTCTTTGGG | TCACAGCGAGGTGAGCCC |
| GP6 | 13254T/C | rs1613662 | ACGTTGGATGATTTCCCAGGAACCTCTGTG<br>ACGTTGGATGATACGCTGTGCACCAGAATG | TACCAACAGAACCACCTTCC |
| F3 | −1208del/ins | — | ACGTTGGATGTTTTGCACAGTTTTATTCTG<br>ACGTTGGATGAGTCAGTCTGCATTTTAAT | CTGTTAAAACAAGTGGTTCAGTA |
| | −603A/G | rs1361600 | ACGTTGGATGTCTTCTACCCCACGAAGGTC<br>ACGTTGGATGATTCCCACCGCCTTTCTCTG | CTACCCCACGAAGGTCAAGAATAC |
| TFP1 | −399C/T | — | ACGTTGGATGTAAAAGTCTGAGGGCTACCG<br>ACGTTGGATGAAGCCTGACACCTGCAATAG | CCGTTGGAGGTCTCTCTTAGTGA |
| | 1006G/A | rs5940 | ACGTTGGATGAAGGAGGCCTAATTAAAACC<br>ACGTTGGATGCATTGCTATAACAAATTCAC | AAAGAAAAGAAAGAAGCAGAGA |

TABLE 6 -continued

| Gene Symbol[1] | Poly-morphism | dbSNP ID[2] | PCR Primers | Extension Primer |
|---|---|---|---|---|
| F2 | 20210G/A | rs1799963 | | |
| F5 | 1691G/A | rs6025 | ACGTTGGATGCTGAAAGGTTACTTCAAGGAC<br>ACGTTGGATGTGGGCTAATAGGACTACTTC | AGGACAAAATACCTGTATTCCT |
| FGB | -854G/A | rs1800791 | ACGTTGGATGCTCACAGACTAAATGAGGCC<br>ACGTTGGATGCACACAAGTGAACAGACAAG | GAGGCCCATTTTCCTTCATTT |
|  | -455G/A | rs1800790 | ACGTTGGATGCATTTAAGCAACATCTTCCC | AAGCAACATCTTCCAGCAAA |
|  | -148C/T | rs1800787 | ACGTTGGATGAACTTCCCATCATTTTGTCC | |
| SERP1NE1 | -675ins/del (5G/4G) | rs1799768 | ACGTTGGATGCTCCGATGATACACGGCTGA<br>ACGTTGGATGAGGTTGTTGACACAAGAGAG | GATACACGGCTGACTCCCC |
| THBD | 1959C/T | rs1042579 | ACGTTGGATGAGTCACAGTCGGTGCCAATG<br>ACGTTGGATGGGTACCTTCGAGTGCATCTG | CACAGTCGGTGCCAATGTGGCGG |
| MTHFR | 677C/T | rs1801133 | ACGTTGGATGATGCCTTCACAAAGCGGAAG<br>ACGTTGGATGCTTGAAGGAGAAGGTGTCTG | GCTGCGTGATGATGAAATCG |
| ACE | in16del/ins | — | | |

Genotyping assays for the 19 candidate polymorphisms: PCR primers (top-forward, bottom-reverse) and extension primers for MALDI-TOF mass specrometry
NOTE:
the ACE indel polymorphism was genotyped using PCR amplification, size fractionation and electrophoretic visualization as described Brief description of the gene products and candidate polymorphisms and the current evidence linking them to a prothrombotic phenotype.

Table 5 Functional phenotypes of candidate genes and polymorphisms and associations with thrombotic outcomes.
Table 6 Primers for genotyping assays.

Gene Products and Candidate Polymorphisms

Platelet Glycoprotein (GP) IIb/IIIa (ITGB3)
Shear mediated platelet thrombus deposition is significantly dependent upon the PLA1/2 polymorphism of the IIIa chain[1], as is responsiveness to epinephrine[2] increased thrombin generation in response to microvascular injury[3] and a prothrombotic phenotype[4].
GP1b_(GP1BA)
The 5T/C substitution (Kozak polymorphism) and the 524 C/T substitution encoding Met145Thr on the GP1b_subunit of the GP1b complex (GP1b_, GP1b_, GPIX and GPV), are associated with increased transcription rate and surface expression of the GP1b complex[5] and a prothrombotic phenotype respectively.[6, 7].
GP1aII/_2_1 integrin (ITGA2)
The 807C/T substitution on the _2 gene regulates the surface density of GPIaIIa (integrin_2_1) and the T allele has prothrombotic associations.[8] c-52T also regulates the surface density of GPIaIIa[9] but has not clinical associations as yet
GP VI (GP6)
Variation in platelet GPVI content alters procoagulant properties[10] and deficiency results in mild bleeding disorder.[11] There is a positive association with MI[12].
Tissue Factor (F3)
2 common haplotypes exist (1208D/603A; 1208I/603G) and 1208D protects against venous thrombosis.[13]
Tissue Factor Pathway Inhibtor (TFPI)
−287C associated with increased TFPI levels and −399T associated with lower post-heparin TFPI levels; therefore −287T and −399T likely prothrombotic during cardiopulmonary bypass.[14]. G1006A also related to post heparin TFPI levels[15].
Factor V (F5)
1691 A (Factor V Leiden) is associated with reduced bleeding after CABG [Donahue, 2003 #3614] and there is a strong association with venous and arterial thrombosis via activated Protein C resistance[15]
Prothrombin (F2)
20210A of 20210 G/A is associated with venous and arterial thrombosis[16]
Fibrinogen_(FGB)
All three polymorphisms are associated with fibrinogen levels but they are in linkage disequilibrium such that −455A is always associated with increased fibrinogen levels (in Caucasians) and the 4 common haplotypes art shown below[17]. However −148T is associated with higher fibrinogen in UK blacks and not 100% in linkage disequilibrium in this group[18]

| −854 | −148 | −455 | |
|---|---|---|---|
| G | C | G | ~40% |
| A | C | G | ~20% |
| G | C | G | ~20% |
| G | T | A | ~20% |

Common haplotypes seen with Fibrinogen_polymorphisms

Thrombomodulin (THBD)
Increased MI risk in blacks only[19], functional/mechanistic basis for this unclear.
Plasminogen Activator Inhibitor—1(PAI-1, SERPINE 1)
Increased levels and increased MI associated with 5G/4G polymorphism[20]
Cathepsin (CTSG)
Associated with increased fibrinogen levels in patients with CAD[21]
Methyltetrahydrofulatereductase (MTHFR)
Homozygotes (freq 0.10) are associated with arterial and venous thrombosis by increasing plasma homocysteine levels[22, 23].

Angiotensin Converting Enzyme (ACE) Indel polymorphism increases risk of venous thrombosis[24][25][26][27].

References

1. Cadroy Y, Sakariassen K, Grandjean H, Thalamas C, Boneu B, Sie P. The effect of platelet PlA polymorphism On experimental thrombus formation in man depends on blood flow and thrombogenic substrate. *Thrombosis & Haemostasis.* 2001; 85:1097-103.
2. Feng D, Lindpaintner K, Larson M G, Rao V S, O'Donnell C J, Lipinska I, Schmitz C, Sutherland P A, Silbershatz H, D'Agostino R B, Mullet J E, Myers R H, Levy D, Tofler G H. Increased platelet aggregability associated with platelet GPIIIa PlA2 polymorphism: the Framingham Offspring Study. *Arteriosclerosis Thrombosis & Vascular Biology.* 1999; 19:1142-7.
3. Undas A, Brummel K, Musial J, Mann K G, Szczeklik A. PI(A2) polymorphism of beta(3) integrins is associated with enhanced thrombin generation and impaired antithrombotic action of aspirin at the site of microvascular injury. *Circulation.* 2001; 104:2666-72.
4. Bray P F. Platelet glycoprotein polymorphisms as risk factors for thrombosis. *Current Opinion in Hematology.* 2000; 7:284-9.
5. Afshar-Kharghan V, Li C Q, Khoshnevis-Asl M, Lopez J A. Kozak sequence polymorphism of the glycoprotein (GP) Ibalpha gene is a major determinant of the plasma membrane levels of the platelet GP 1b-IX-V complex. *Blood.* 1999; 94:186-91.
6. Gonzalez-Conejero R, Lozano M L, Rivera J, Corral J, Iniesta J A, Moraleda J M, Vicente V. Polymorphisms of platelet membrane glycoprotein 1b associated with arterial thrombotic disease. *Blood.* 1998; 92:2771-6.
7. Murata M, Malsubara Y, Kawano Zama T, Aoki N, Yoshino H, Watanabe G, Ishikawa K, Ikeda Y. Coronary artery disease and polymorphisms in a receptor mediating shear stress-dependent platelet activation. *Circulation.* 1997; 96:3281-6.
8. Santos S, Kunicki T J, Kroll H, Haberbosch W, Gardemann A. Association of the platelet glycoprotein 1a C807T gene polymorphism with nonfatal myocardial infarction in younger patients. *Blood.* 1999; 93:2449-53.
9. Jacquelin B, Tarantino M D, Kritzik M, Rozenshteyn D, Koziol J A, Nurden A T, Kunicki T J. Allele-dependent transcriptional regulation of the human integrin alpha2 gene. *Blood.* 2001; 97:1721-6.
10. Furibata K, Clemetson K J, Deguchi H, Kunicki T J Variation in human platelet glycoprotein VI content modulates glycoprotein VI-specific prothrombinase activity. *Arteriosclerosis, Thrombosis & Vascular Biology.* 2001; 21:1857-63.
11. Moroi M, Jung S M, Okuma M, Shinmyozu K. A patient with platelets deficient in glycoprotein VI that lack both collagen-induced aggregation and adhesion. *Journal of Clinical Investigation.* 1989; 84:1440-5.
12. dCroft S A, Samani N J, Teare M D, Hampton K K, Steeds R P, Charmer K S, Daly M E. Novel platelet membrane glycoprotein VI dimorphism a risk factor for myocardial infarction. [comment]. *Circulation.* 2001; 104:1459-63.
13. Arnaud E, Barbalat V, Nicaud V, Cambien F, Evans A, Morrison C, Arveiler D, Luc G, Ruidavets J B, Emmerich J, Fiessinger J N, Aiach M. Polymorphisms in the 5' regulatory region of the tissue factor gene and the risk of myocardial infarction and venous thromboembolism: the ECTIM and PATHROS studies. Etude Cas-Temoins de l'Infarctus du Myocarde. Paris Thrombosis case-control Study. *Arteriosclerosis. Thrombosis & Vascular Biology.* 2000; 20:892-8
14. Moatti D, Haidar B, Fumeron F, Gauci L, Boudvillain O, Seknadji F, Oliver V, Aumont M C, de Prost D. A new T-287C polymorphism in the 5' regulatory region of the tissue factor pathway inhibitor gene Association study of the T-287C and C-399T polymorphisms with coronary artery disease and plasma TFPI levels. *Thrombosis & Haemostasis.* 2000; 84:24-4-9.
15. Amini-Nekoo A, Futers T S, Moia M, Mannucci P M, Grant P J, Ariens R A. Analysis of the tissue factor pathway inhibitor gene and antigen levels in relation to venous thrombosis *British Journal of Haematology.* 2001; 113:537-43.
16. Doggen C J, Cats V M, Bertina R M, Rosendaal F R. Interaction of coagulation defects and cardiovascular risk factors: increased risk of myocardial infarction associated with factor V Leiden or prothrombin 20210A [comment]. *Circulation.* 1998; 97:1037-41.
17. Green F R. Fibrinogen polymorphisms and atherothrombotic disease. *Annals of the New York Academy of Sciences.* 21101; 936:549-59.
18. Cook D G, Cappuccio F P, Atkinson R W, Wicks P D, Chitolie A, Nakandakare E R, Sagnella G A, Humphries S E. Ethnic differences in fibrinogen levels: the role of factors and the beta-fibrinogen gene. *American Journal of Epidemiology.* 2001; 153:799-806
19. Wu K K, Aleksic N, Ahn C, Boerwinkle E, Folsom A R, Juneja H, Atherosclerosis Risk in Communities Study I. Thrombomodulin Ala455Val polymorphism and risk of coronary heart disease. *Circulation.* 2001; 103:1386-9.
20. Eriksson P, Kallin B. van't Hooll F M, Bavenholm F, Harnsten A. Allele-specific increase in basal transcription of the plasminogen-activator inhibitor 1 gene is associated with myocardial infarction. *Proceedings of the National Academy of Sciences of the United States of America.* 1995; 92:1851-5.
21. Herrmann S M, Funke-Kaiser H, Schmidt-Petersen K, Nicaud V, Gautier-Bertrand M, Evans A, Kee F, Arveiler D, Morrison C, Orzechowski R D, Elbaz A, Amarenco P, Cambien F, Paul M. Characterization of polymorphic structure of cathepsin G gene: role in cardiovascular and cerebrovascular diseases. *Arteriosclerosis, Thrombosis & Vascular Biology.* 2001; 21:1538-43.
22. Arruda V R, von Zuben P M, Chiaparini L C, Annichino-Bizzacchi J M, Costa F F. The mutation Ala677->Val in the methylene tetrahydrofolate reductase gene: a risk factor for arterial disease and venous thrombosis. *Thrombosis & Haemostasis.* 1997; 77:818-21.
23. Gemmati D, Serino M L, Trivellato C, Fiorini S, Scapoli G L. C677T substitution in the methylenetetrahydrofolate reductase gene as a risk factor for venous Thrombosis and arterial disease in selected patients. *Haematologica.* 1999; 8-4:824.8.
24. Philipp C S, Dilley A, Saidi P, Evatt B, Austin H, Zawadsky J, Harwood D, Ellingsen D, Barnhart E, Phillips D J, Hooper W C. Deletion polymorphism in the angiotensin-converting enzyme gene as a thrombophilic risk factor after hip arthroplasty. *Thrombosis & Haemostasis.* 1998; 80:869-73.
25. Hooper W C, Dowling N F, Wenger N K, Dilley A, Ellingsen D, Evatt B L. Relationship of venous thromboembolism and myocardial infarction with the renin-angiotensin system in African-Americans. *American Journal of Hematology.* 2002; 70:1-8.

26. Lu Y, Hui R, Zhao Y. Insertion/deletion polymorphsim of the angiotensin I converting enzyme gene and pulmonary thromboembolism in Chinese population. *Chung-Hua Chieh Ho Ho Hu His Tsa Chih Chinese Journal of Tuberculosis & Respiratory Diseases*. 2001; 24:265-8.

27. Isbir C S, Akgun S, Yilmaz H, Civelek A, Ak K, Tekeli A, Agachan B, Cobanoglu A. Is then a role of angiotensin-converting enzyme gene polymorphism in the failure of arteriovenous femoral shunts for hemodialysis? *Annals of Vascular Surgery*. 2001; 15:443-6.

EXAMPLE 2

Experimental Details
Study Population

This analysis is a sub-study of the Perioperative Genetics and Safety Outcomes Study (PEGASUS), an ongoing IRB approved, prospective, longitudinal study at Duke University Medical Center, where 3,149 patients have been prospectively enrolled and consented to have clinical and genetic data analyzed in relation to perioperative outcomes. The current sub-study targets 2075 patients undergoing primary elective CABG surgery using CPB during a pre-specified period when detailed perioperative serum creatinine and dialysis data was systematically and prospectively collected. Patients were excluded from analysis who died within 2 days of surgery (n=42), were receiving dialysis prior to or after surgery (n=38), or for whom creatinine data at all time points was not available (n=227). Of the final 1,768 patients examined, 1,464 were Caucasian, 207 were African American, and 97 were of another race; due to small numbers in each of the "other" race categories, the analysis was limited to Caucasians and African Americans.

Clinical Data Collection

The primary outcome variable selected was peak fractional change in postoperative serum creatinine (% ΔCr), defined as percent difference between preoperative serum creatinine (CrPre) and highest of the daily in-hospital postoperative values ($Cr_{max}Post$); this is a commonly used, validated continuous variable reflecting relative reduction in renal filtration function (Andersson et al, Thorac. Cardiovasc. Surg. 41(4):237-241 (1993)). Serum creatinine was determined using a dry slide enzymatic reflectance technique (Vitros 950, Johnson and Johnson, New Brunswick, N.J.) with a normal range of 44-133 μmol/L (0.5-1.4 mg/dl). Preoperative clinical covariate data includes demographic variables and pre-existing comorbidities (Table 7). Intra- and postoperative variables include duration of CPB, duration of aortic crossclamp, number of aortacoronary bypass grafts, blood product usage, requirement for inotropic drugs and/or intra-aortic balloon pump (IABP) counterpulsation (Table 7). Use of agents with potential renal effects (e.g., intravenous dopamine, furosemide and mannitol) was recorded and taken into account during analysis, but not regulated, since these agents have not demonstrated significant beneficial effects in the setting of cardiac surgery (Conger, Am. J. Kidney Dis. 26(4):565-576 (1995), Vijayan and Miller, Semin. Nephrol. 18(5):523-532 (1998), Galley, Lancet 356(9248):2112-2113 (2000), Bellomo et al, Lancet 356(9248):2139-2143 (2000)). Each CPB circuit was primed with mannitol (250 ml 20% solution).

TABLE 7

Patient, Procedural, and Renal Function Characteristics

|  | Caucasian (n = 1464) | African American |
|---|---|---|
| Demographic Variables | | |
| Age (years) | 64 +/− 11 | 63 +/− 11 |
| Body mass index (kg/m$^2$) | 29.7 +/− 14.1 | 31.4 +/− 18.5 |
| Female (%) | 26 | 50 |
| Weight (kg) | 86.2 +/− 19.1 | 84.2 +/− 18.2 |
| Preoperative Comorbidities | | |
| Carotid bruit (%) | 6 | 5 |
| Chronic Steroid Therapy (%) | 1 | 3 |
| Hannan Mortality Risk Score* | 0.025 +/− 0.029 | 0.028 +/− 0.036 |
| History of congestive heart failure (%) | 16 | 21 |
| History of diabetes (%) | 32 | 42 |
| History of hypertension (%) | 65 | 82 |
| Preoperative inotropic drug infusion(s)$^\infty$ (%) | 1 | 1 |
| Preoperative intraaortic balloon counterpulsation (%) | 1 | 2 |
| History of myocardial infarction (%) | 27 | 28 |
| History of obstructive lung disease (%) | 12 | 8 |
| History of peripheral vascular disease (%) | 13 | 18 |
| History of stroke (%) | 6 | 10 |
| Preoperative ejection fraction (%) | 52 +/− 14 | 49 +/− 14 |
| Preoperative hematocrit (%) | 39 +/− 7 | 37 +/− 8 |
| Preoperative renal dysfunction (Cr ≥1.5 mg/dl) (%) | 7 | 11 |
| Unstable angina prior to surgery (%) | 68 | 74 |
| Procedure | | |
| Duration of aortic crossclamping (min) | 63 +/− 31 | 59 +/− 28 |
| Duration of cardiopulmonary bypass (min) | 114 +/− 46 | 110 +/− 46 |
| Number of coronary artery bypass grafts | 3.2 +/− 0.9 | 3.1 +− 0.8 |
| Postoperative Course | | |
| Inotropic drug infusion(s)** upon arrival in intensive | 21 | 27 |
| Postoperative intraaortic balloon counterpulsation (%) | 1 | 1 |
| Transfusion^ (%) | 23 | 25 |

TABLE 7-continued

Patient, Procedural, and Renal Function Characteristics

|  | Caucasian (n = 1464) | African American |
|---|---|---|
| Renal Function Variables | | |
| Peak postoperative serum creatinine (mg/dL) | 1.4 +/− 0.8 | 1.7 +/− 1.2 |
| Rise in serum creatinine (mg/dL) | 0.3 +/− 2.1 | 0.3 +/− 1.0 |
| Peak postoperative fractional creatinine rise[#] | 30 +/− 52 | 34 +/− 44 |
| Postoperative estimated creatinine clearance[@] | 73 +/− 31 | 63 +/− 28 |
| Fall in creatinine clearance[@] (ml/min) | −15 +/− 21 | −15 +/− 20 |
| Preoperative estimated creatinine clearance[@] (ml/min) | 88 +/− 34 | 79 +/− 33 |
| Preoperative serum creatinine (mg/dL) | 1.1 +/− 0.5 | 1.3 +/− 1.0 |

Abbreviations:

[^]Transfusion - a marker of perioperative transfusion (>2 units packed red cells and at least one other blood product within 24 hours of surgery)
[#]Peak percentage change in postoperative creatinine (% ΔCr) defined as the difference between preoperative and peak postoperative values represented as a percentage of the preoperative value.
[*]The Hannan Score is a risk factor score for in-hospital mortality following CABG surgery, identified by Hannan et al., in the New York State population (Hannan et al, JAMA 264(21): 2768-2774 (1990)).
[**]Inotropic drug use, defined as postoperative infusion of either dopamine >5 μg/kg/min and/or dobutamine >5 μg/kg/min, or epinephrine >0.03 μg/kg/min.
[@]Using the Cockroft-Gault equation (Cockcroft and Gault, Nephron 16(1): 31-41 (1976)), preoperative, lowest postoperative, and change in creatinine clearance (CrClPre) were calculated using preoperative and peak postoperative serum creatinine values.

Rationale for Candidate Polymorphism Selection

Twelve polymorphisms in 7 candidate genes were prospectively chosen, based on a priori hypotheses about their probable role in postoperative renal injury; detailed gene and polymorphism information for this study can be found at anesthesia.duhs.duke.edu/pegasus/renal/1/(Table 8). Genes selected included angiotensin converting enzyme (ACE), angiotensinogen (AGT), angiotensin receptor 1 (AGTR 1), endothelial constitutive nitric oxide synthase (eNOS, also referred to as NOS 3), IL6 (n=3), tumor necrosis factor alpha (TNFα, n=3), and apoE (n=2). Additionally, 58 unlinked markers were used to assess and control for population admixture, as previously described (Pritchard et al, Genetics 155(2):945-959 (2000)).

TABLE 8

Association of Genetic Polymorphisms with Peak Postoperative Rise in Serum Creatinine (%ΔCr)

| | | | Caucasian | | African American | |
|---|---|---|---|---|---|---|
| Gene | Polymorphism | Genotype | Freq (%) | %ΔCr (+/−SD) | Freq (%) | %ΔCr (+/−SD) |
| Vasomotor regulation genes | | | | | | |
| Angiotensin Converting Enzyme | Intron 16 Deletion(D)/ Insertion(I) | DD | 32 | 27 (39) | 41 | 32 (44) |
| | | DI | 46 | 27 (60) | 46 | 36 (51) |
| | | II | 22 | 29 (40) | 13 | 33 (27) |
| Angiotensinogen | T842C | TT | 35 | 26 (45) | 7 | 23 (46) |
| | | TC | 47 | 28 (40) | 30 | 31 (48) |
| | | CC | 18 | 36 (82) | 63 | 37 (43) |
| Angiotensin Receptor 1 | A1166C | AA | 50 | 27 (43) | 83 | 31 (43) |
| | | CA | 40 | 29 (45) | 14 | 35 (43) |
| | | CC | 10 | 36 (96) | 3 | 29 (29) |
| Endothelial Constitutive Nitric Oxide Synthase | G894T | GG | 42 | 29 (50) | 74 | 34 (46) |
| | | TG | 44 | 28 (55) | 23 | 31 (36) |
| | | TT | 13 | 33 (48) | 3 | 52 (68) |
| Proinflammatory genes | | | | | | |
| Interleukin 6 | G − 174C | GG | 26 | 30 (74) | 75 | 30 (42) |
| | | GC | 55 | 30 (46) | 23 | 55 (58) |
| | | CC | 19 | 24 (34) | 2 | 12 (11) |
| Interleukin 6 | G − 572C | GG | 91 | 28 (45) | 76 | 35 (44) |
| | | GC | 8 | 33 (98) | 23 | 29 (43) |
| | | CC | 1 | 27 (—) | 1 | −39 (—) |
| Interleukin 6 | G597A | GG | 29 | 31 (72) | 74 | 30 (40) |
| | | GA | 54 | 29 (44) | 24 | 48 (54) |
| | | AA | 17 | 24 (34) | 2 | 12 (11) |
| Tumor Necrosis Factor α | G + 488A | GG | 87 | 30 (53) | 94 | 35 (46) |
| | | GA | 12 | 21 (30) | 6 | 24 (48) |
| | | AA | 1 | 26 (19) | 0 | |
| Tumor Necrosis Factor α | G − 308A | GG | 69 | 29 (46) | 77 | 33 (46) |
| | | GA | 28 | 28 (62) | 21 | 34 (39) |
| | | AA | 3 | 35 (45) | 2 | 28 (10) |
| Tumor Necrosis Factor α | G − 376A | GG | 97 | 28 (49) | 99 | 34 (45) |
| | | GA | 2 | 22 (24) | 1 | 14(20) |
| | | AA | 1 | 11 (—) | 0 | |

TABLE 8-continued

Association of Genetic Polymorphisms with Peak Postoperative Rise in Serum Creatinine (%ΔCr)

| Gene | Polymorphism | Genotype | Caucasian Freq (%) | Caucasian %ΔCr (+/−SD) | African American Freq (%) | African American %ΔCr (+/−SD) |
|---|---|---|---|---|---|---|
| Other gene polymorphisms previously associated with acute renal injury | | | | | | |
| Apolipoprotein E | T448C | TT | 78 | 29 (53) | 63 | 35 (41) |
| | (APOE ε4) | CT | 21 | 27 (49) | 33 | 37 (52) |
| | | CC | 2 | 27 (35) | 4 | 32 (62) |
| Apolipoprotein E | C586T | CC | 84 | 26 (39) | 85 | 32 (45) |
| | (APOE ε2) | CT | 15 | 25 (41) | 14 | 36 (44) |
| | | TT | 1 | 47 (62) | 1 | 29 (—) |

Abbreviations:
%ΔCr—Peak percentage change in postoperative creatinine is defined as the difference between the preoperative and peak postoperative values and represented as a percentage of the preoperative value.
SD—standard deviation Isolation of Genomic DNA and Genotype Analysis Blood was collected immediately prior to surgery; genomic DNA extraction was performed using the Puregene™ system (Gentra Systems, Minneapolis, Minn.). Most genotyping assays for single nucleotide polymorphisms were conducted at Agencourt Bioscience Corporation (Beverly, Mass.) by Matrix Assisted Laser Desorption/Ionization, Time-Of-Flight (MALDI-TOF) mass spectrometry, using the Sequenom™ MassARRAY™ system (Sequenom, San Diego, Calif.) (Sun et al, Nucleic Acids Res. 28(12):E68 (2000)). Primers used to amplify, and details of, the polymorphisms can be found at anesthesia.duhs.duke.edu/pegasus/renal/1/(Tables 9-11), Genotyping accuracy of the Sequenom™ MassARRAY™ system was estimated at 99.6% (Gabriel et al, Science 296(5576):2225-2229 (2002)); reproducibility of genotyping was validated to be >99% by scoring a panel of 6 polymorphisms in 100 randomly selected patients using direct sequencing on an ABI3700 capillary sequencer (Applied Biosystems, Foster City, Calif.). Angiotensin converting enzyme (ACE) deletion and insertion (D/I) alleles were identified on the basis of polymerase chain reaction amplification of the respective fragments from the intron 16 of the ACE gene, followed by size-fractionation via electrophoresis as previously described (Rigat et al, J. Clin. Invest. 86(4):1343-1346 (1990). Results were scored by 2 independent investigators blinded to the clinical phenotype. After completion of genotype analysis, genetic samples were linked to covariate and phenotypic variables in a relational database with extensive quality control features.

TABLE 9

Pairwise linkage disequilibrium between markers in IL6 and TNFα genes.

| | Allele frequency +/−D' | | Race |
|---|---|---|---|
| IL6 SNP | −572G/C | −597G/A | |
| G−174C | −0.46* | +0.42* | Caucasians |
| G−572C | | −0.43* | |
| G−597A | | | |
| G−174C | −0.25 NS | +0.5* | African Americans |
| G−572C | | −0.2 NS | |
| G−597A | | | |

TABLE 9-continued

Pairwise linkage disequilibrium between markers in IL6 and TNFα genes.

| | Allele frequency +/−D' | | Race |
|---|---|---|---|
| TNFA SNP | −308G/A | +123(in1)G/A | |
| G−376A | −0.72* | −0.55* | Caucasians |
| G−308A | | −0.33* | |
| G+123A | | | |
| G−376A | −1.00* | −1.00* | African Americans |
| G−308A | | −0.16 NS | |
| G+123A | | | |

TABLE 10

Pairwise Linkage Disequilibrium between Markers in IL 6 and TNFα Genes

| Gene Polymorphism | Linkage Disequilibrium (+/−D') | | Race |
|---|---|---|---|
| IL 6 | G−572C | G−597A | |
| G−174C | −0.46* | +0.42* | Caucasians |
| G−572C | | −0.43* | |
| G−174C | −0.25 NS | +0.5* | African Americans |
| G−572C | | −0.2 NS | |
| TNFα | G−308A | G488A | |
| G−376A | −0.72* | −0.55* | Caucasians |
| G−308A | | −0.33* | |
| G−376A | −1.00* | −1.00* | African Americans |
| G−308A | | −0.16 NS | |

D': Lewontin's D';
*p < 0.01;
NS: non-significant

TABLE 11

Genotyping Assays for the 12 Candidate Gene Polymorphisms
PCR primers (top-forward, bottom-reverse) and extension primers for MALDI-TOF mass spectrometry assays

| Gene Symbol | Polymorphism | PCR Primers | Extension Primer |
|---|---|---|---|
| ACE | Intron 15 D/I* | CTGGAGACCACTCCCATCCTTTCT<br>GATGTGGCCATCACATTCGTCAGAT | — |
| AGT | T842C | ACGTTGGATGTGTGACAGGATGGAAGACTG<br>ACGTTGGATGGTGGACGTAGGTGTTGAAAG | AAGACTGGCTGCTCCCTGA |
| AGTR1 | A1166C | ACGTTGGATGATTCCTCTGCAGCACTTCAC<br>ACGTTGGATGCGGTTCAGTCCACATAATGC | GCACTTCACTACCAAATGAGC |
| eNOS | G894T | ACGTTGGATGAAACGGTCGCTTCGACGTGC<br>ACGTTGGATGATCCCTTTGGTGCTCACGTG | GCTGCAGGCCCCAGATGA |
| IL6 | G-174C | ACGTTGGATGAGCCTCAATGACGACCTAAG<br>ACGTTGGATGGATTGTGCAATGTGACGTCC | TTTCCCCCTAGTTGTGTCTTGC |
| IL6 | G-572C | ACGTTGGATGACGCCTTGAAGTAACTGCAC<br>ACGTTGGATGTCTTCTGTGTTCTGGCTCTC | CAGGCAGTCTACAACAGCC |
| IL6 | G-597A | ACGTTGGATGACGCCTTGAAGTAACTGCAC<br>ACGTTGGATGTCTTCTGTGTTCTGGCTCTC | AAGTAACTGCACGAAATTTGAGG |
| TNFα | G488A | ACGTTGGATGGAAAGATGTGCGCTGATAGG<br>ACGTTGGATGCTTGCCACATCTCTTTCTGC | GGGAGGGATGGAGAGAAAAAAAC |
| TNFα | G-308A | ACGTTGGATGGATTTGTGTGTAGGACCCTG<br>ACGTTGGATGGGGTCCCCAAAAGAAATGGAG | ACCCTGGAGGCTGAACCCCGTCC |
| TNFα | G-376A | ACGTTGGATGCTCCCAGTTCTAGTTCTATC<br>ACGTTGGATGTTGCCTCCATTTCTTTTGGG | TTCCTGCATCCTGTCTGGAA |
| APOE | T448C | ACGTTGGATGTGTCCAAGGAGCTGCAGGC<br>ACGTTGGATGTCGGTGCTCTGGCCGAGCAT | GCGGACATGGAGGACGTG |
| APOE | C586T | ACGTTGGATGACATTCCCCTTCCACGCTTG<br>ACGTTGGATGTAGAGGTCTTTTGACCACCC | GAATGGAGGAGGGTGTCTG |

*NOTE:
The ACE indel polymorphism was genotyped using PCR amplification, size fractionation and electrophoretic visualization as described; PCR-polymerase chain reaction Statistical Analysis Descriptive statistics, including allele frequency, Hardy-Weinberg equilibrium, and linkage disequilibrium, were calculated for all 12 candidate polymorphisms (Tables 8-11). Due to the presence of some rare alleles, prior to analysis genotypes homozygous for the candidate poymorphisms were combined with heterozygote carriers; consequently analyses were based on 2 genotypic classes for each candidate polymorphism, reflecting the presence (1 or 2 copies) or absence of the candidate allele. Since self-reported race has been found to be an independent predictor of postoperative acute renal injury (Conlon et al, Nephrol. Dial Transplant. 14(5):1158-1162 (1999)), and population admixture is a potential confounder of genetic association studies, an a priori decision was made to evaluate Caucasian and African American groups separately if a race effect was confirmed.

For analyses of the effect of specific clinical and general variables on postoperative acute renal injury, first clinical models were developed using perioperative and demographic variables previously shown to account for variation in postoperative acute renal injury (Conlon et al, Nephrol. Dial Transplant. 14(5):1158-1162 (1999), Chertow et al, Am. J. Med. 104(4):343-348 (1998)). Then separate analyses were performed for each polymorphism to test the null hypothesis of no association between genotype and postoperative acute renal injury. Polymorphisms were also combined to investigate possible two-way gene interactions. A multiple linear regression model for % ΔCr was fit including 12 candidate gene polymorphisms as main effects and important interaction terms; stepwise backward elimination was used to obtain a simpler model. To protect against multiple comparisons, particularly for gene-gene interactions, the α level was set at 0.05 for primary allele associations, and 0.001 for secondary pair-wise interactions (with $0.001<p<0.01$ being considered a trend). The resulting combination of polymorphisms constituted the final genetic model. Projected mean % ΔCr for all possible genotypic combinations was generated by this model. Finally, an overall model, combining variables from the genetic model with those already identified in the clinical model, was also fit to determine the extent to which genetic polymorphisms account for variation in postoperative acute renal injury beyond that explained by clinical variables. Initial univariate and two-way interaction queries performed to test the primary hypothesis used all available genetic and/or clinical data.

To further investigate the relationship of race and postoperative acute renal injury, relative population weights (determined by population structure analysis employing 54 unlinked genetic polymorphisms) were used to test for association between race and postoperative acute renal injury, as previously described (Pritchard et al, Genetics 155(2):945-959 (2000)). Statistical analysis was performed using SAS/Genetics system version 8.02 (SAS Inc, Cary, N.C.). Continuous variables are described as mean+/−standard deviation (SD); categorical variables are described as percentages. Throughout this Example, all genetic polymorphisms are described using the following convention: wild type (major) allele first (left), followed by nucleotide number, then minor allele on the right.

Results

Demographic and intraoperative characteristics of the study population are similar to those reported in other cardiac surgery populations (Table 7) (Andersson et al, Thorac. Cardiovasc. Surg. 41(4):237-241 (1993)). Specifically, renal injury was common, demonstrated by more than half of the patients sustaining >30% postoperative creatinine rise; this is equivalent to 25% reduction in creatinine clearance (Cockcroft and Gault, Nephron 16(1):31-41 (1976)). Linkage within genes was identified among IL6 and TNF polymorphisms (Tables 9-11); while the IL6 linkage has already been reported (Park et al, Exp. Mol. Med. 35(2): 76-82 (2003)), the TNFα linkage is novel.

In contrast to some forms of acute renal failure (e.g., rhabdomyolysis-related renal injury where 93% can be explained) (Ward, Arch. Intern. Med. 148(7):1553-1557 (1988)), clinical predictors of post-cardiac surgery acute renal dysfunction explain very little of the variability in renal injury (overall $R^2$=0.028 in the present study). However, analysis by race (a known risk factor for renal injury) (Conlon et al, Nephrol. Dial Transplant. 14(5):1158-1162 (1999)) did improve overall clinical prediction ($R^2$=0.03 Caucasians; $R^2$=0.13 African Americans), whether ethnic background was determined by self-reporting or via genetic structure analysis (Pritchard et al, Genetics 155(2):945-959 (2000)); in this study, self-reported race proved the stronger model.

Figure 2A:
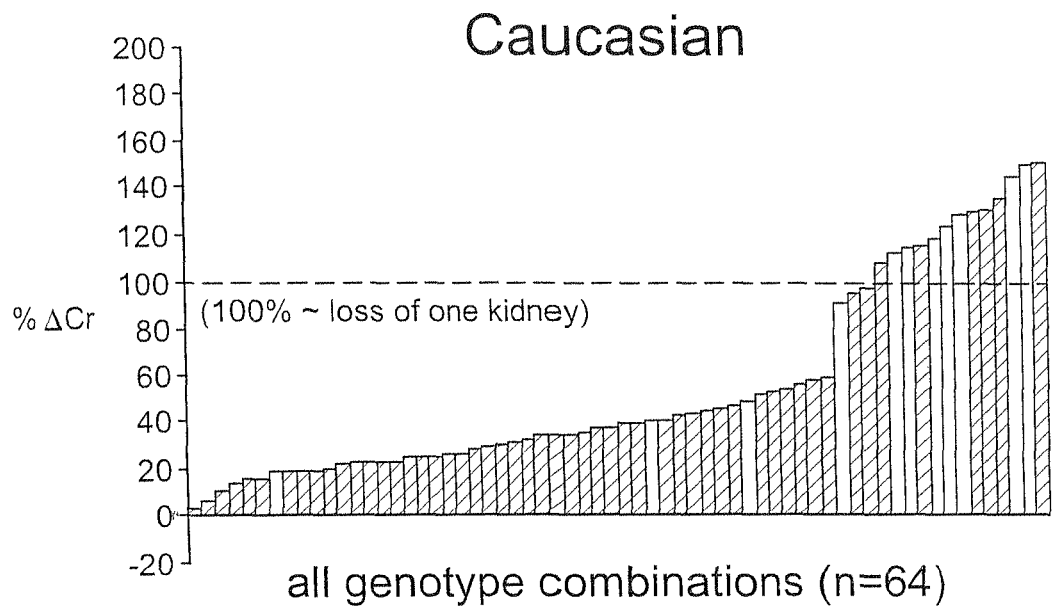
FIGS. 2A and 2B: Results of the model predicting peak postoperative serum creatinine rise (% ΔCr) after aortocoronary surgery for all pairwise gene polymorphism combinations identified in multivariable genetic predictive models for Caucasian (FIG. 2A) and African American (FIG. 2B) patients. Six polymorphisms in Caucasians and 4 in African Americans result in sixty-four ($2^6$) and sixteen ($2^4$) different possible combinations, respectively. Combinations observed in the study population are shown as black bars. The dashed line represents 2-fold (100%) increase in predicted postoperative serum creatinine rise, roughly equivalent to the loss of one kidney.
Figure 2B:
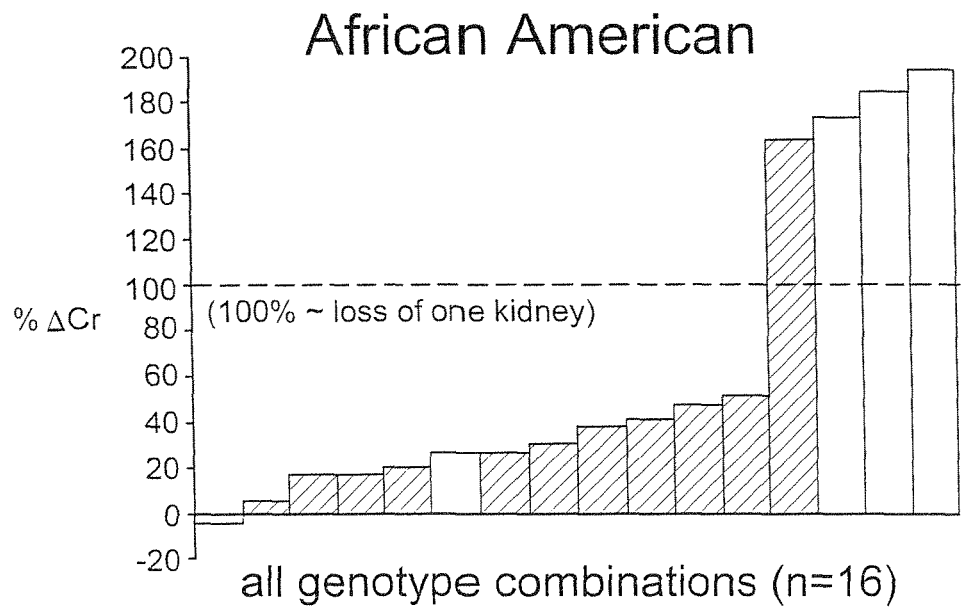
Figure 3A:
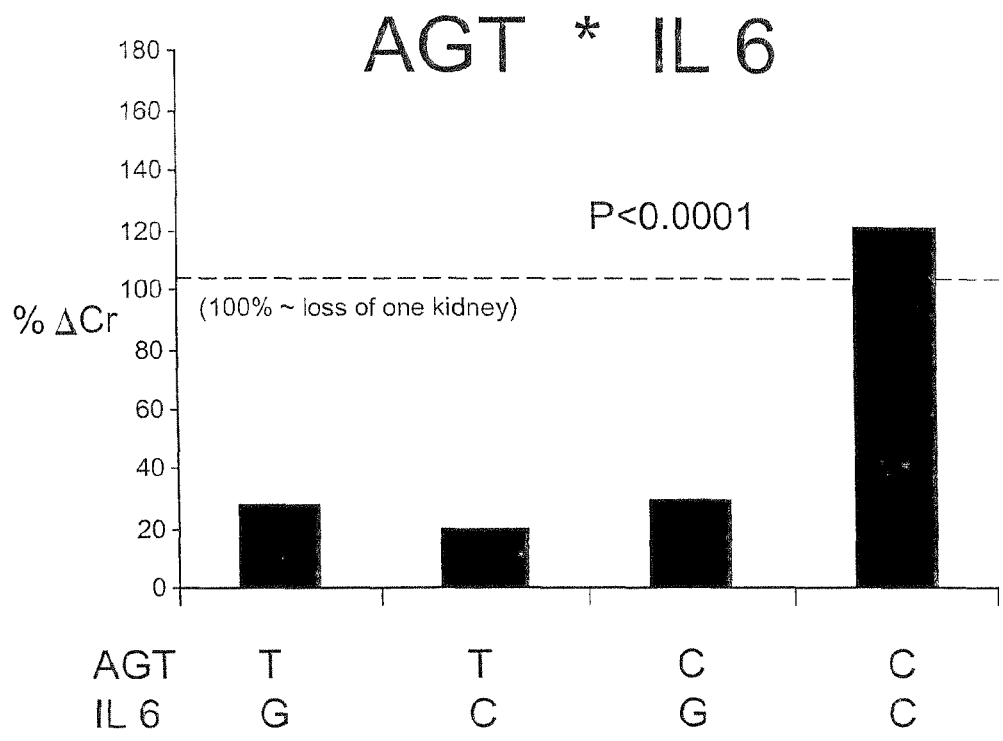
FIGS. 3A and 3B: Differences in predicted peak postoperative serum creatinine rise after coronary bypass surgery for two gene polymorphism interactions identified in the multivariable genetic predictive models. The dashed line represents 2-fold (100%) increase in predicted renal injury, roughly equivalent to the loss of one kidney. Abbreviations: AGT—angiotensinogen T842C polymorphism, IL6—interleukin 6 G-572C polymorphism, eNOS—endothelial nitric oxide synthase G894T polymorphism, ACE—angiotensin converting enzyme insertion/deletion polymorphism.
Figure 3B:
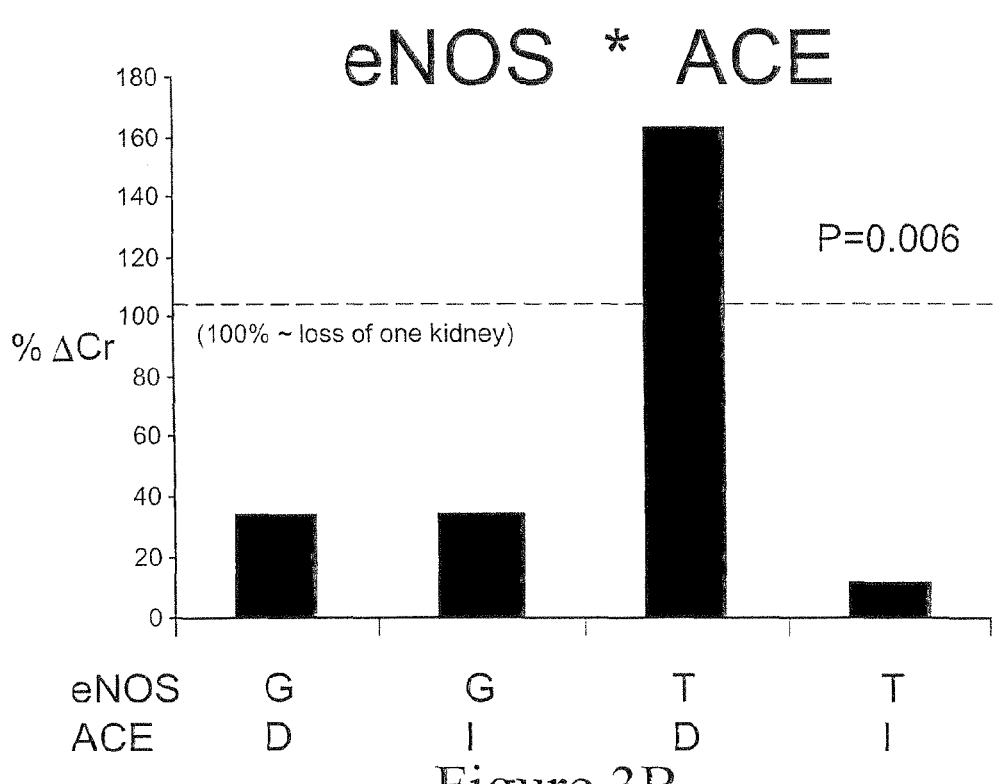
Figure 4A:
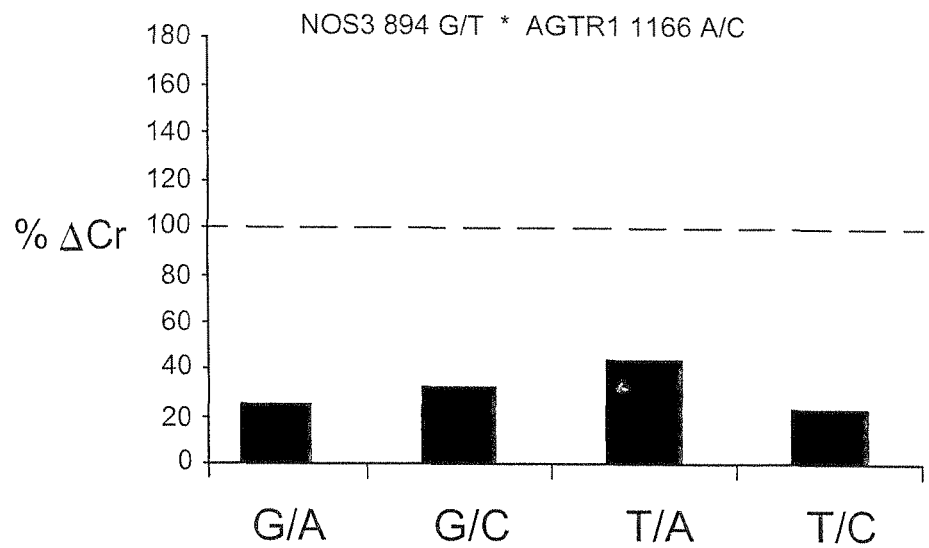
FIGS. 4A-4G: Graphic representation of individual two-way gene polymorphism interactions in the multivariable genetic only models for predicted peak postoperative serum creatinine rise (% ΔCr) after aortocoronary surgery. The dashed line represents a 2-fold (100%) increase in predicted renal injury.
Figure 4B:
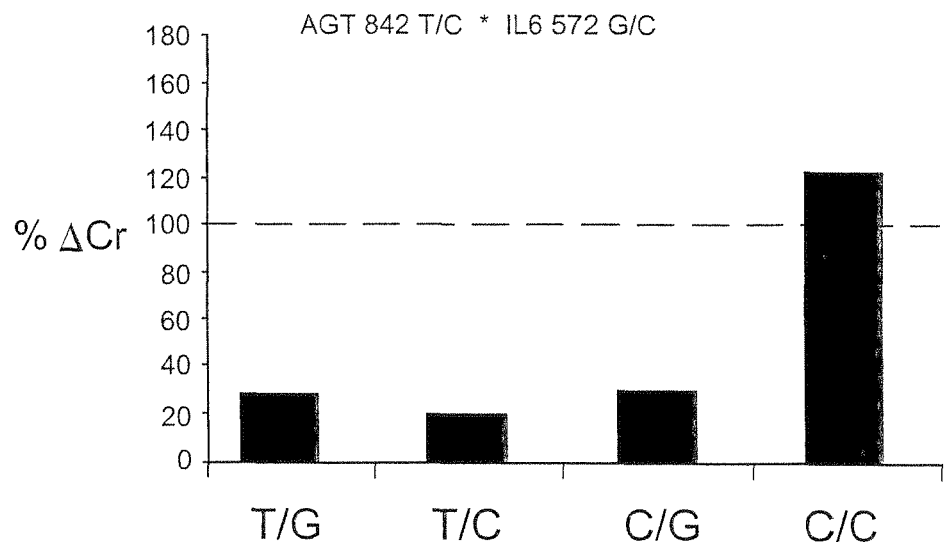
Figure 4C:
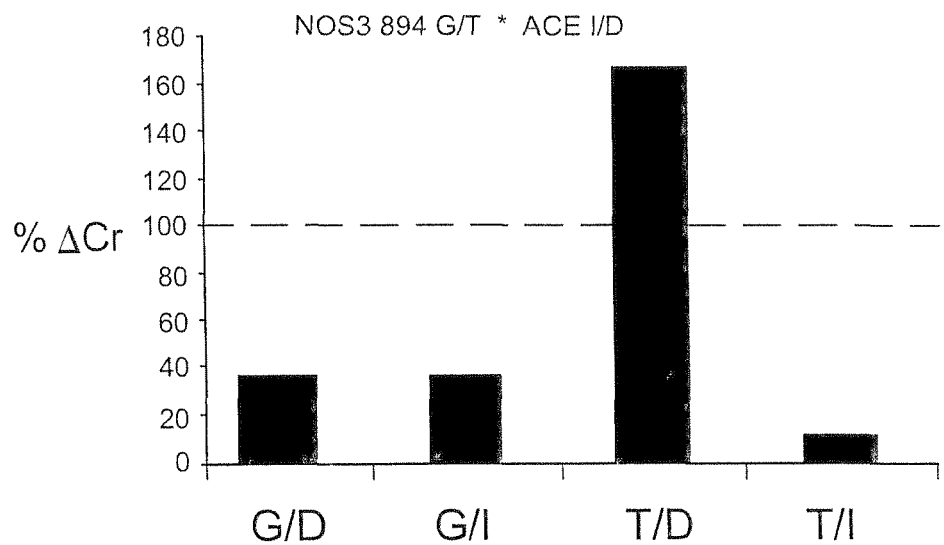
Figure 4D:
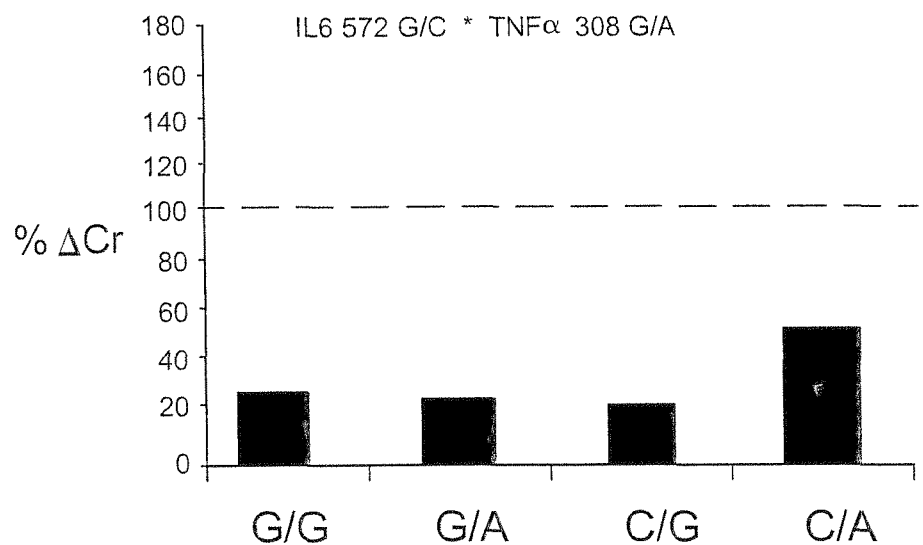
Figure 4E:
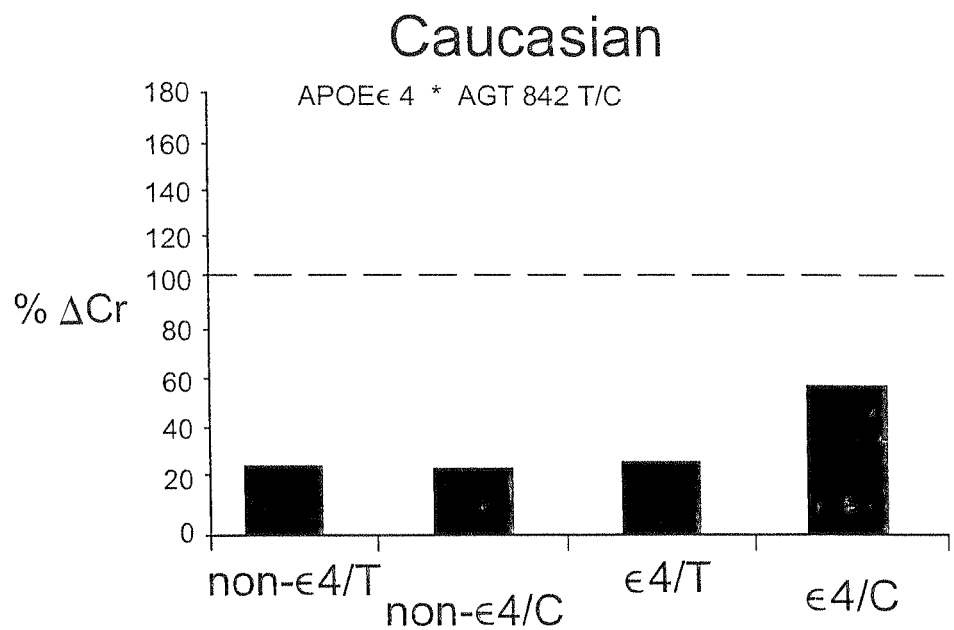
Figure 4F:
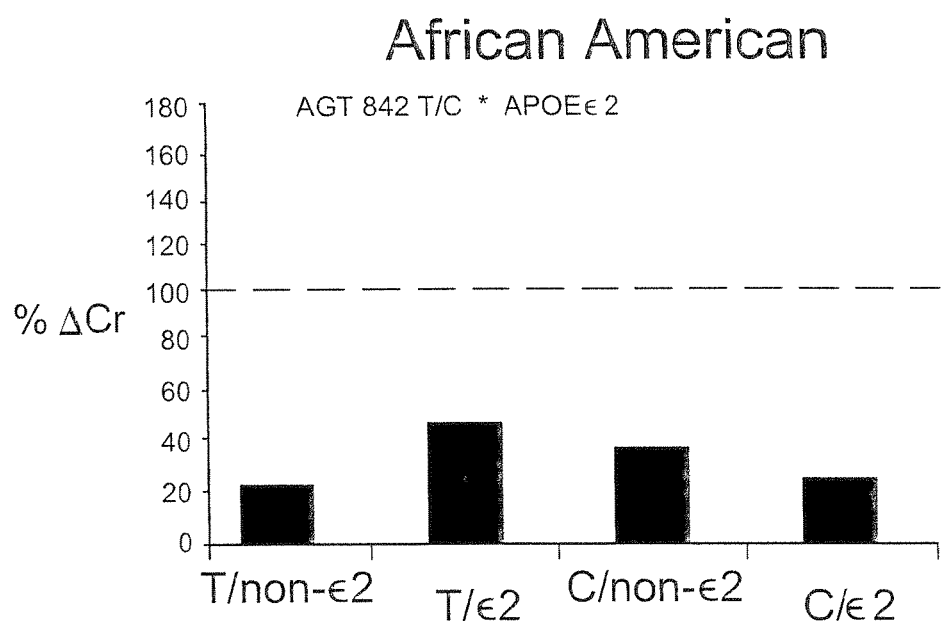
Figure 4G:
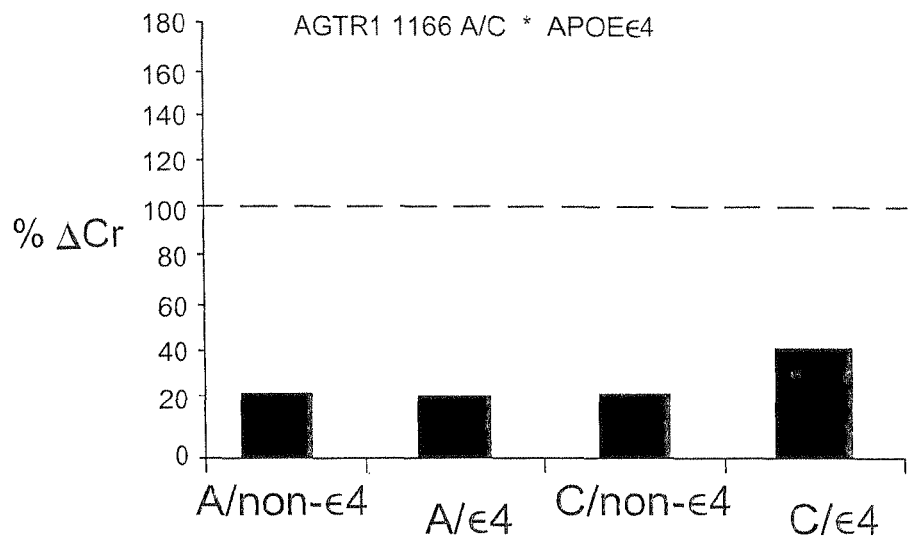

After analyzing clinical predictors, attention was next turned to the predictive value of genetic variables alone. Average postoperative acute renal injury (% ΔCr) associated with each of the 12 candidate polymorphisms is detailed in Table 8. In the multivariable analysis, no primary effects were identified, but 6 polymorphisms (6 for Caucasians; 4 for African Americans) demonstrated significant association with % ΔCr in two-way interactions between alleles (Tables 12 and 13). (See also FIG. 2.) A spectrum of renal injuries are predicted by the model; some allele combinations predict major renal reductions in renal filtration, equivalent to >50% decrease in creatinine clearance (FIG. 4). Raw data shown in FIG. 3 demonstrates association of specific high-risk polymorphism interactions with renal injury, mean % ΔCr values for all allele interactions are presented in FIG. 4. Overall genetic factors predict 7% of the variability in acute renal injury for Caucasians and 10% for African Americans (see Tables 12 and 13) occurring after aortocoronary surgery, a figure which is surprisingly better than clinical predictors alone. Finally, combination of clinical and genetic models are approximately additive, significantly enhancing prediction of postoperative acute renal injury compared to clinical-alone models. In fact 11% of acute renal injury variability in Caucasians and 20% for African Americans (Tables 12 and 13) is predicted with the combined model.

TABLE 12

Genetic, Clinical, and Combined Genetic and Clinical Multivariable Risk Factor Models Predicting Peak Postoperative Serum Creatinine Rise in 1464 Caucasians after Aortocoronary Surgery.

|  |  | F-value | P value |
|---|---|---|---|
| A. Clinical Factors Alone Model ($r^2$ = 0.03) | | | |
| Clinical factors | age (years) | 7.2 | 0.007 |
|  | weight (kg) | 4.15 | <0.0001 |
|  | history of obstructive pulmonary disease | 6.55 | 0.01 |
|  | preoperative creatinine (mg/dL) | 7.3 | 0.007 |
|  | postoperative inotropic drug infusion | 2.75 | 0.05 |
|  | duration of cardiopulmonary bypass (min) | 4.43 | 0.04 |
| B. Genetics Alone Model ($r^2$ = 0.067) | | | |
| Polymorphism | eNOS | 1.89 | 0.17 |
|  | TNF α | 1.91 | 0.17 |
|  | IL 6 | 20.04 | <0.0001 |
|  | AGTR1 | 0.04 | 0.84 |
|  | AGT | 32.19 | <0.0001 |
|  | APOE ϵ2 | 6.94 | 0.009 |
| Interactions | eNOS * AGTR1 | 7.55 | 0.006 |
|  | IL 6 * TNF α | 3.58 | 0.05 |
|  | AGT * IL 6 | 23.44 | <0.0001 |
|  | APOE ϵ2 * AGT | 4.49 | 0.03 |
|  | AGTR1 * APOE ϵ2 | 5.97 | 0.02 |
| C. Combined Clinical and Genetic Model ($r^2$ = 0.11) | | | |
| Polymorphism | eNOS | 2.05 | 0.15 |
|  | TNF α | 1.80 | 0.18 |
|  | IL 6 | 22.04 | <0.0001 |
|  | AGTR1 | 0.03 | 0.86 |
|  | AGT | 30.05 | <0.0001 |
|  | APOE ϵ2 | 5.80 | 0.02 |
| Interactions | eNOS * AGTR1 | 6.39 | 0.01 |
|  | IL 6 * TNF α | 3.84 | 0.05 |
|  | AGT * IL 6 | 23.25 | <0.0001 |
|  | APOE ϵ2 * AGT | 2.76 | 0.09 |
|  | AGTR1 * APOE ϵ2 | 5.74 | 0.01 |
| Clinical factors | age (years) | 2.91 | 0.08 |
|  | weight (kg) | 15.94 | <0.0001 |
|  | history of obstructive pulmonary disease | 4.32 | 0.04 |
|  | preoperative creatinine (mg/dL) | 9.57 | 0.0002 |
|  | postoperative inotropic drug infusion | 4.91 | 0.03 |
|  | duration of cardiopulmonary bypass (min) | 5.87 | 0.02 |

Abbreviations: eNOS—endothelial nitric oxide synthase G894T polymorphism, TNF α—tumor necrosis factor α G-308A polymorphism, IL 6—IL 6 G-572C polymorphism, AGTR1—angiotensin receptor type 1 A1166C polymorphism, AGT—angiotensinogen T842C polymorphism, APOE ϵ2—apolipoprotein E C586T polymorphism

TABLE 13

Genetic, Clinical, and Combined Genetic and Clinical Multivariable Risk Factor Models Predicting Peak Postoperative Serum Creatinine Rise in 207 African Americans after Aortocoronary Surgery.

|  |  | F-value | P value |
|---|---|---|---|
| A. Clinical Factors Alone Model ($r^2$ = 0.132) | | | |
| Clinical factors | history of obstructive pulmonary disease | 3.78 | 0.05 |
|  | history of peripheral vascular disease | 16.33 | <0.0001 |
|  | history of chronic steroid therapy | 7.14 | 0.008 |
|  | body mass index (kg/m2) | 6.85 | 0.01 |
| B. Genetics Alone Model ($r^2$ = 0.132) | | | |
| Polymorphism | eNOS | 4.29 | 0.04 |
|  | AGT | 0.00 | 0.99 |
|  | ACE D/I | 8.40 | 0.004 |
|  | APOE ϵ4 | 1.02 | 0.32 |
| Interactions | eNOS * ACE | 7.77 | 0.006 |
|  | AGT * APOE ϵ4 | 4.72 | 0.03 |
| C. Combined Clinical and Genetic Model ($r^2$ = 0.204) | | | |
| Polymorphism | eNOS | 2.83 | 0.09 |
|  | AGT | 0.03 | 0.87 |
|  | ACE D/I | 7.00 | 0.009 |
|  | APOE ϵ4 | 0.61 | 0.44 |
| Interactions | eNOS * ACE | 7.28 | 0.008 |
|  | AGT * APOE ϵ4 | 3.45 | 0.06 |

TABLE 13-continued

Genetic, Clinical, and Combined Genetic and Clinical Multivariable
Risk Factor Models Predicting Peak Postoperative Serum Creatinine
Rise in 207 African Americans after Aortocoronary Surgery.

|  |  | F-value | P value |
|---|---|---|---|
| Clinical factors | history of obstructive pulmonary disease | 3.17 | 0.08 |
|  | history of peripheral vascular disease | 9.33 | 0.003 |
|  | history of chronic steroid therapy | 0.73 | 0.39 |
|  | body mass index (kg/m2) | 5.31 | 0.02 |

Abbreviations: eNOS—endothelial nitric oxide synthase G894T polymorphism, AGT—angiotensinogen T842C polymorphism, ACE D/I—angiotensin converting enzyme deletion/insertion polymorphism, APOE ε4—apolipoprotein E C448T polymorphism.

Conclusions

In spite of the relatively common occurrence of acute renal failure after surgery, the best clinical models presently available only poorly predict postoperative renal dysfunction. The present study identifies important genetic underpinnings of this disorder. In Caucasians, the combined possession of two polymorphisms (AGT 894C and IL6-572C, a variant pattern that occurs in 6% of Caucasians) predicts major post-operative renal injury, being associated with an average peak serum creatinine rise of 121% (p<0.0001). This is equivalent to a 55% reduction in renal filtration, or the loss (at least temporarily) of more than one kidney, 4 times greater than average for the overall population. These findings emphasize the importance of studying genes in multiple converging biological pathways in understanding predictors of complex disease such as acute renal injury.

Cardiac surgery provokes a vigorous inflammatory response that contributes to renal insult (Laffey et al, Anesthesiology 97:215-252 (2002)). Inflammation is a rapid, highly amplified, humoral and cellular response that can occur both systemically and locally in the kidney. Endotoxin and circulating inflammatory cytokines peak 4-24 hours after cardiopulmonary bypass (Schmartz et al, J. Thorac. Cardiovasc. Surg. 125(1):184-190 (2003), Aydin et al, J. Thorac. Cardiovasc. Surg. 125(4):843-848 (2003)) and have been directly associated with acute renal injury (Cunningham et al, J. Immunol. 168(11):5817-5823 (2002), Meldrum et al, J. Surg. Res. 85(2):185-199 (1999)). Supporting this effect of intermediate markers, in the present study inheriting the AGT 894C and IL6-572C alleles together is highly related to acute renal injury in Caucasians (p<0.0001); both of these alleles are proinflammatory and have been associated with increased intermediate biological markers (IL6 protein levels) compared with their wild type allele Wang et al, Yi Chuan Xue Bao 30(10):978-982 (2003), Kelberman et al, Biochim. Biophys. Acta 1688(2):160-167 (2004)). In a single allele association study, Gaudino and colleagues noted increased postoperative renal dysfunction in carriers of the −174C polymorphism in 111 coronary bypass patients (Gaudino et al, J. Thorac. Cardiovasc. Surg. 126(4):1107-1112 (2003)). While in the present study, the IL6-572C and not the −174C was related to acute renal injury, the findings of Gaudino and colleagues support the present findings since significant linkage disequilibrium was noted between these 2 alleles in Caucasians, indicating they are included in a haplotype block (Tables 9-11). Further confirming the present findings, both of these IL6 polymorphisms have been associated with greater rises in IL 6 protein levels after cardiac surgery (Kelberman et al, Biochim. Biophys. Acta 1688(2):160-167 (2004), Burzotta et al, Am. J. Cardiol. 88(10):1125-1128 (2001), Brull et al, Arterioscler. Thromb. Vasc. Biol. 21(9):1458-1463 (2001), Gaudino et al, Circulation 108(Suppl 1):11195-199 (2003), Galley et al, Br. J. Anaesth. 91(3):424-426 (2003)). Other proinflammatory polymorphisms may also contribute to renal injury; the TNFα-308A allele has been associated with increased production of IL6 protein (Heesen et al, Crit. Care Med. 30(3):664-669 (2002)). A weak association (p=0.05) was noted, towards greater renal injury with, IL6-572C and TNFα-308A alleles in the present study, with patients possessing both enduring 2 times greater creatinine rise compared to other patients. In summary, the main finding of the present study is that a 'high risk' proinflammatory polymorphism combination commonly seen in Caucasians presenting for heart surgery predicts a severe postoperative acute renal injury.

In addition to being pro-inflammatory, cardiac surgery also results in atheroembolism and ischemia-reperfusion injury, both potentially important contributors to a cumulative perioperative renal insult. Once renal injury occurs, intense renal vasoconstriction and exaggerated responsiveness to vasoconstrictor agents is observed, effects that takes several weeks to resolve (Myers et al, Kidney Int. 18(4):495-504 (1980)). In the context of the precarious oxygen supply to the renal medulla, subtle polymorphism-related differences in the regulation of renal perfusion may increase the extent of renal injury and delay recovery. In the above study, all 4 pairwise allele-interactions predicting renal injury (i.e., eNOS*AGTR 1, AGT*IL6 and AGTR 1*APOE ε2 in Caucasians, and eNOS*ACE in African Americans; see Tables 12 & 13) involve at least 1 polymorphism associated with increased renal vascular responsiveness; in 2 interactions (eNOS*AGTR 1 and eNOS*ACE), both polymorphisms have these effects (Hopkins et al, J. Hypertens. 14(2):199-207 (1996), Amant et al, Circulation 96(1):56-60 (1997), Henrion et al, J. Vasc. Res. 35(5):356-362 (1998), Philip et al, Circulation 99(24):3096-3098 (1999)). Overall, the greatest magnitude of renal injury is observed in African. American subjects, where possession of two vasoconstrictor polymorphisms (the ACE D and eNOS 894T alleles) is associated with mean peak creatinine rise of 162.5% from preoperative levels (p=0.008), equivalent to greater than 60% reduction in glomerular filtration. Should such a renal vulnerability be confirmed in a larger population, this trend of borderline statistical significance would be a finding of major clinical significance. The renin-angiotensin system (RAS) system and eNOS are central to regulation of renal medullary blood flow (Cowley et al, Am. J. Physiol. Regal. Integr. Comp. Physiol. 284(6):R1355-1369 (2003), Arendshorst et al, J. Am. Soc. Nephrol. 10(Suppl. 11):S149-161 (1999)); polymorphisms of these pathways that augment vascular tone may contribute to medullary ischemia during the initial insult, but also throughout the recovery phase of an acute renal injury.

The remaining gene to achieve a trend toward significance in the present study is the APOE ε2 allele. In 2 previous single polymorphism association studies (Chew et al, Anesthesiology 93(2):325-331 (2000), Mackensen et al, Ann. Thor. Surg. 78(2):520-526 (2004)), an association was observed between APOE polymorphisms and renal injury in cardiac surgery patients. While the precise role of APOE in acute renal injury remains to be determined, recent evidence suggests a modulating role of apoE on the inflammatory cascade, with different responses among the 3 apoE polymorphisms (Brown et al, Free Radic. Biol. Med. 32(11):1071-1075 (2002)).

In summary, in the present study reveals a role for inflammatory and vasoconstrictor genes in predicing acute renal injury after heart surgery. These findings support mechanisms thought to contribute to renal injury in many other acute and chronic renal disorders across medicine, reinforcing the usefulness of this robust perioperative model. While strict criteria were used in this study, caution is still appropriate when generalizing from any genetic association study since limitations exist. First, additional prospective studies will be required to confirm the results. In addition, other important alleles, either not considered as primary candidate polymorphisms or in linkage disequilibrium with studied polymorphisms (Jorde, Genome Res. 10(10):1435-1444 (2000)), may not have been tested in the present study. Furthermore, the instant findings do not presume that the causative polymorphism has been identified since the variants could be in linkage disequilibrium with one or more causation polymorphisms; indeed, examination of candidate polymorphisms in Caucasians and African Americans identifies haplotype blocks within both the IL 6 and TNF a genes. However, this new information can be used to predict renal injury nevertheless even if only a genetic marker.

EXAMPLE 3

Experimental Details
Study Population

The patients enrolled in this study were part of the Perioperative Genetics and Safety Outcomes Study (PEGASUS), an ongoing Institutional Review Board approved, prospective, longitudinal study at Duke University Medical Center. Patients undergoing cardiac surgery gave written informed consent to have their clinical and genetic data analyzed in relation to perioperative outcomes. This study of stroke outcomes examined patients undergoing coronary artery bypass graft (CABG), valvular, or combined CABG/valve surgery utilizing CPB, during a specified period, in whom definitive data on the presence or absence of stroke was gathered.

Clinical Data Collection

Ischemic stroke was the primary outcome variable. During the study period, all patients with suspected stroke (defined as any new focal abnormality on neurologic examination occurring within one week of surgery) underwent evaluation by an independent neurologist and confirmatory brain imaging (magnetic resonance [MRI] or computerized tomography [CT]). Patients with cerebral hemorrhage or generalized encephalopathy were specifically excluded. Fulfillment of these criteria were confirmed after independent review of patient hospital records. Preoperative clinical covariate data including age, sex, race, and pre-existing co-morbidities considered important to stroke (Table 14) were also recorded and analyzed.

TABLE 14

Patient Demographics and Intraoperative Characteristics

| Variable | No Stroke n = 2066 | Stroke n = 38 | P-value* |
|---|---|---|---|
| Age (Years) | 63 ± 12 | 68 ± 10 | 0.003+ |
| Male Gender (%) | 65.9 | 60.5 | 0.493 |
| Caucasian (%) | 82.3 | 78.9 | 0.667 |
| Ejection Fraction (%) | 51 ± 14 | 48 ± 12 | 0.212 |
| Unstable Angina (%) | 61.6 | 62.9 | 0.999 |
| Pre-operative Stroke/TIA (%) | 7.1 | 8.6 | 0.735 |
| Carotid Bruit (%) | 6.5 | 5.7 | 0.999 |
| Peripheral Vascular Disease (%) | 13.7 | 14.3 | 0.999 |
| Diabetes (%) | 30.3 | 37.1 | 0.458 |
| Congestive Heart Failure (%) | 28.1 | 22.9 | 0.573 |

TABLE 14-continued

Patient Demographics and Intraoperative Characteristics

| Variable | No Stroke n = 2066 | Stroke n = 38 | P-value* |
|---|---|---|---|
| Hypertension (%) | 66.5 | 71.4 | 0.593 |
| COPD (%) | 11.3 | 17.1 | 0.279 |
| Obesity (%) | 9.1 | 2.7 | 0.249 |
| Ever Smoked (%) | 48.6 | 40.0 | 0.394 |
| Salicylates (%) | 75.7 | 62.9 | 0.110 |
| Preoperative Beta Blocker (%) | 69.2 | 48.6 | 0.011+ |
| Redo Cardiac Surgery (%) | 7.2 | 10.5 | 0.520 |
| Any Valve Surgery (%) | 18.0 | 23.7 | 0.393 |
| CPB Time (min) | 125 ± 57 | 146 ± 69 | 0.164 |
| Aortic Cross-Clamp Time (min) | 71 ± 41 | 81 ± 45 | 0.289 |
| Number of Grafts | 3.1 ± 0.9 | 3.2 ± 0.8 | 0.516 |

Values represent mean ± standard deviation.
Abbreviations: TIA = transient ischemic attack; Beta blocker = beta-adrenergic antagonist therapy; COPD = chronic obstructive pulmonary disease; CPB = cardiopulmonary bypass; Stroke = ischemic stroke.
*P-values are from Wilcoxon Rank-Sum test for continuous measures, and from exact Chi-Squared test for categorical (%) characteristics.
+Note:
Preoperative beta blocker became non-significant when added to the genetic model, whereas age remained significant.

Candidate Polymorphism Selection

Based on a literature review regarding stroke in experimental, clinical, and cardiac surgical settings, 26 SNPs were identified as primary candidates for analysis. The 26 SNPs represented 13 genes, which were classified on the basis of biological function into categories of coagulation, inflammation, and lipid metabolism (Table 15). The coagulation and inflammatory categories were chosen based on extensive literature supporting a role of thrombosis and inflammation in stroke whereas the lipid metabolism category (specifically, apolipoprotein E) was chosen because of its previous demonstration of a relationship to other neurologic disorders, including post-cardiac surgery cognitive dysfunction (Tardiff et al, Ann. Thorac. Surg. 64:715-720 (1997)).

TABLE 15

Polymorphisms Investigated in Multivariable Modeling to Determine Their Relationship to Post-Cardiac Surgery Ischemic Stroke.

| Functional Category | SNP ID[1] | Gene Symbol[2] (Name) | Alleles (major/minor) |
|---|---|---|---|
| Coagulation | RS1799963 | F2 (Prothrombin) | 20210G/A |
| | RS1361600 | F3 (Tissue factor) | −603A/G |
| | P021[3] | F3 (Tissue factor) | −1208indel (18 bp) |
| | RS6025 | F5 (Factor V) | 1691G/A |
| | RS1800787 | FGB (Fibrinogen beta) | −148C/T |
| | RS1800790 | FGB (Fibrinogen beta) | −455G/A |
| | RS1800791 | FGB (Fibrinogen beta) | −854G/A |
| | RS1800792 | FGG (Fibrinogen gamma) | −649A/G |
| | RS2243093 | GP1BA (Glycoprotein Ib alpha) | −5 T/C |
| | RS6065 | GP1BA (Glycoprotein Ib alpha) | 524C/T |
| | RS1800198 | ITGA2 (Glycoprotein IaIIa) | 807C/T |
| | RS28095 | ITGA2 (Glycoprotein IaIIa) | −52C/T |
| | RS5918 | ITGB3 (Glycoprotein IIIa) | 1565T/C |
| | RS1799768 | PAI-1 (SERPINE 1) | −675indel (5G/4G) |
| | RS2227631 | PAI-1 (SERPINE 1) | −844A/G |
| Inflammation | RS1205 | CRP (C reactive protein) | 3′UTR 1846C/T |
| | RS1800947 | CRP (C reactive protein) | 1059G/C |
| | RS1800795 | IL6 (Interleukin 6) | −174G/C |
| | RS1800796 | IL6 (Interleukin 6) | −572G/C |
| | RS1800797 | IL6 (Interleukin 6) | −597G/A |
| | RS1800610 | TNFA (TNF alpha) | +488G/A |
| | RS1800629 | TNFA (TNF alpha) | −308G/A |

TABLE 15-continued

Polymorphisms Investigated in Multivariable Modeling to Determine Their Relationship to Post-Cardiac Surgery Ischemic Stroke.

| Functional Category | SNP ID[1] | Gene Symbol[2] (Name) | Alleles (major/minor) |
|---|---|---|---|
| | RS1800750 | TNFA (TNF alpha) | −376G/A |
| | RS361525 | TNFA (TNF alpha) | −238G/A |
| Lipid metabolism | RS429358 | APO E (Apolipoprotein E) | 448T/C |
| | RS7412 | APO E (Apolipoprotein E) | 586C/T |

[1]From NCBI's dbSNP public database (ncbi.nlm.nih.gov/SNP/)
[2]From OMIM (catalogue of human genes and genetic disorders; ncbi.nlm.nih.gov/OMIM/)
[3]Duke polymorphism ID Number; UTR = untranslated region Isolation of Genomic DNA and Genotype Analysis Whole blood was collected preoperatively with genomic DNA extraction subsequently performed using the Puregene™ system (Gentra Systems, Minneapolis, Minn.). Genotyping assays for SNPs were conducted at Agencourt Bioscience Corporation (Beverly, Mass.) by Matrix Assisted Laser Desorption/Ionization Time-Of-Flight (MALDI-TOF) mass spectrometry, using the Sequenom™ MassARRAY™ system (Sequenom, San Diego, Calif.) (Sun et al, Nucleic Acids Res. 28(12):E68 (2000)). Primers used and polymorphism details can be found at anesthesia.duhs.duke.edu/pegasus/stroke/1/. (See Table 16.) Genotyping accuracy of the Sequenom™ MassARRAY™ system was estimated at 99.6% (Gabriel et al, Science 296(5576):2225-2229 (2002)). Using direct sequencing on an ABI3700 capillary sequencer (Applied Biosystems, Foster City, Calif.), genotyping reproducibility in this study was validated to be >99% by scoring a panel of six polymorphisms in 100 randomly selected patients. After completion of genotype analysis, genetic results were linked to covariate and phenotypic variables in a relational database.

TABLE 16

Genotyping Assays for the Candidate Gene Polymorphisms
http://anesthesia.duhs.duke.edu/pegasus/stroke/1/website table 1.htm

| Gene Symbol[1] (Name) | Chromosome | SNP ID[2] | Alleles (major/minor) | Genotyping Assay Primers[3] |
|---|---|---|---|---|
| F2 (Prothrombin) | 11P11-q12 | RS1799963 | 20210G/A | ACGTTGGATGTGGAACCAATCCCGTGAAAG ACGTTGGATGAGAGAGCTGCCCATGAATAG CCAATAAAAGTGACTCTCAGC |
| F3 (Tissue factor) | 1p22-p21 | RS1361600 | −603A/G | ACGTTGGATGTCTTCTACCCCACGAAGGTC ACGTTGGATGATTCCCACCGCCTTTCTCCTG CTACCCCACGAAGGTCAAGAATAC |
| | | P021[4] | −1208indel(18 bp) | ACGTTGGATGTTTTGCACAGTTTTATTCTG ACGTTGGATGAGTCAGTCTTGCATTTTAAT CTGTTAAAACAAGTGGTTCAGTA |
| F5 (Factor V) | 1q23 | RS6025 | 1691G/A | ACGTTGGATGCTGAAAGGTTACTTCAAGGAC ACGTTGGATGTGGGCTAATAGGACTACTTC AGGACAAAATACCTGTATTCCT |
| FGB (Fibrinogen beta) | 4q28 | RS1800787 | −148C/T | ACGTTGGATGCATTTAAGCAACATCTTCCC ACGTTGGATGAACTTCCCATCATTTTGTCC AAGCAACATCTTCCCAGCAAA |
| | | RS1800790 | −455G/A | ACGTTGGATGGCTTATGTTTTCTGACAATG ACGTTGGATGTCATAGAATAGGGTATGAAT CATAATTCTATTTCAAAAGGGGC |
| | | RS1800791 | −854G/A | ACGTTGGATGCTCACAGACTAAATGAGGCC ACGTTGGATGCACACAAGTGAACAGACAAG GAGGCCCATTTTCCTTCATTT |
| FGG (Fibrinogen gamma) | 4q28 | RS1800792 | −649A/G | ACGTTGGATGATGCCCACCTTCAGACAAAG ACGTTGGATGCCTCTGTGTCAACCATGTTC GAGCTCAAAAGCTCCCTGAG |
| GP1BA (Glycoprotein Ib alpha) | 17pter-p12 | RS2243093 | −5 T/C | ACGTTGGATGATCCACTCAAGGCTCCCTTG ACGTTGGATGTTGGCAGCAGGAGCAGCAAG GGCTCCCTTGCCCACAGG |
| | | RS6065 | 524C/T | ACGTTGGATGTGTTGTTAGCCAGACTGAGC ACGTTGGATGAAGGCAATGAGCTGAAGACC TCCAGCTTGGGTGTGGGC |
| ITGA2 (Glycoprotein IaIIa | 5p11.12 | RS1800198 | 807C/T | ACGTTGGATGTGGCCTATTAGCACCAAAAC ACGTTGGATGAGACATCCCAATATGGTGGG TTACCTTGCATATTGAATTGCTCC |
| | | RS3906 | −52C/T | ACGTTGGATGGATCCGGTGTTTGCGGAATC ACGTTGGATGAGGGAAAAGTTTCTGGGCAG CGGAATCAGGAGGGGCGGGC |
| ITGB3 (Glycoprotein IIIa | 17q21.32 | RS5918 | 1565T/C | ACGTTGGATGCCTTCAGCAGATTCTCCTTC ACGTTGGATGTTGCTGGACTTCTCTTTGGG TCACAGCGAGGTGAGCCC |

TABLE 16 -continued

Genotyping Assays for the Candidate Gene Polymorphisms
http://anesthesia.duhs.duke.edu/pegasus/stroke/1/website_table_1.htm

| Gene Symbol[1] (Name) | Chromosome | SNP ID[2] | Alleles (major/minor) | Genotyping Assay Primers[3] |
|---|---|---|---|---|
| SERPINE1 (Plasminogen activator inhibitor-1) | 7q21.3-q22 | RS1799768 | -675indel(5G/4G) | ACGTTGGATGCTCCGATGATACACGGCTGA ACGTTGGATGAGGTTGTTGACACAAGAGAG GATACACGGCTGACTCCCC |
| | | RS2227631 | -844A/G | ACGTTGGATGAAGGAAACAGGAGACCAACG ACGTTGGATGGAGGATAAAGGACAAGCTGC GACCAACGTGTAAGTTTCACTTC |
| CRP (C reactive protein) | 1q21-q23 | RS1205 | 3'UTR 1846C/T | ACGTTGGATGGCCATCTTGTTTGCCACATG ACGTTGGATGGTTTGTCAATCCCTTGGCTC TTGTTTGCCACATGGAGAGAGACT |
| | | RS1800947 | 1059G/C | ACGTTGGATGGAAATGTGAACATGTGGGAC ACGTTGGATGAGGACATTAGGACTGAAGGG TGTGAACATGTGGGACTTTGTGCT |
| IL6 (Interleukin 6) | 7P21 | RS1800795 | -174G/C | ACGTTGGATGAGCCTCAATGACGACCTAAG ACGTTGGATGGATTGTGCAATGTGACGTCC TTTCCCCCTAGTTGTGTCTTGC |
| | | RS1800796 | -572G/C | ACGTTGGATGACGCCTTGAAGTAACTGCAC ACGTTGGATGTCTTCTGTGTTCTGGCTCTC CAGGCAGTCTACAACAGCC |
| | | RS1800797 | -597G/A | ACGTTGGATGACGCCTTGAAGTAACTGCAC ACGTTGGATGTCTTCTGTGTTCTGGCTCTC AAGTAACTGCACGAAATTTGAGG |
| TNFA (TNF alpha) | 6p21.3 | RS1800610 | +488G/A | ACGTTGGATGGAAAGATGTGCGCTGATAGG ACGTTGGATGCTTGCCACATCTCTTTCTGC GGGAGGGATGGAGAGAAAAAAAC |
| | | RS1800629 | -308G/A | ACGTTGGATGGATTTGTGTGTAGGACCCTG ACGTTGGATGGGTCCCCAAAAGAAATGGAG ACCCTGGAGGCTGAACCCCGTCC |
| | | RS1800750 | -376G/A | ACGTTGGATGCTCCCAGTTCTAGTTCTATC ACGTTGGATGTTGCCTCCATTTCTTTTGGG TTCCTGCATCCTGTCTGGAA |
| | | RS361525 | -238G/A | ACGTTGGATGACACAAATCAGTCAGTGGCC ACGTTGGATGATCAAGGATACCCCTCACAC GAAGACCCCCTCGGAATC |
| APOE (Apolipoprotein E) | 19q13.2 | RS429358 | 448T/C | ACGTTGGATGTGTCCAAGGAGCTGCAGGC ACGTTGGATGTGCGGTGCTCTGGCCGAGCAT GCGGACATGGAGGACGTG |
| | | RS7412 | 586C/T | ACGTTGGATGACATTCCCCTTCCACGCTTG ACGTTGGATGTAGAGGTCTTTTGACCACCC GAATGGAGGAGGGTGTCTG |

[1]From the Online Mendelian Inheritance in Man (OMIM) public database (http://www.ncbi.nlm.nih.gov/OMIM)
[2]From NCBI's dbSNP public database (httn://www.ncbi.nlm.nih.Lrov/SNP/)
[3]MALDI-TOF mass spectrometry genotyping assays: from top to bottom-forward PCR primer, reverse PCR primer, extension primer.
[4]Duke polymorphism ID number.

Statistical Analysis

For purposes of association tests, heterozygotes were combined with homozygotes for the minor frequency allele. Consequently, association analyses for each candidate polymorphism were based on two genotypic classes, distinguished by the presence of at least one copy of the minor allele.

Pearson Chi square tests were used to test for independence between stroke and race or gender. Association between SNP genotype and self-declared race was investigated using Chi square tests. In addition, the presence of cryptic population structure was investigated using 58 unlinked, non-candidate SNPs to fit a hierarchical model of population structure (Humphries and Morgan, Lancet Neurol. 3(4):227-235 (2004)).

Chi square tests for independence between stroke and SNP genotype were computed for each of the 26 candidate SNPs. Tests for genetic effects of a pair of SNPs were investigated separately within each functional category by distinguishing genotypes bearing at least one minor allele at both SNPs. This particular partition of genotypes yielded a 2×2 table of genotype by stroke thereby allowing a test for independence with individual SNPs. There exist three other partitions of genotypes based on joint presence or absence of the minor allele in pairs of SNPs and tests were carried out for independence on these genotype partitions as well. After these genetic association tests, a logistic regression model was used to test the joint independent effects of significant SNPs and age, a factor repeatedly shown to be of importance to post-cardiac surgery stroke (Roach et al, N. Engl. J. Med. 335(25):185701863 (1996), Newman et al, Circulation 94(9 Suppl):II74-II80 (1996), Cipollone et al, JAMA 291(18): 2221-2228 (2004), Gaudino et al, J. Thorac. Cardiovasc. Surg. 126(4):1107-1112 (2003)). In addition, beta blocker therapy (Armory et al, J. Cardiothorac. Vasc. Anesth. 16(3): 270-277 (2002)), race, and gender were tested separately in follow-up analyses with the final genetic model that included age.

Because the analysis strategy employed many separate tests of independence, an adjustment of observed p-values was required to account for this multiple testing. Random permutation analysis was used to adjust p-values (Chasman et al, JAMA 291(23):2821-2827 (2004)). 5000 copies of the data set were generated, randomly reassigning stroke events to study subjects, thereby disassociating genotype from stroke events in the data. For each permutation, p-values were calculated for all four genotype partitions of each pair of SNPs. For each genotype partition, the smallest p-value was retained to estimate the distribution of 5000 "smallest" p-values under the null hypothesis of no association. An adjusted p-value was computed as the fraction of permutation p-values that were smaller than the observed p-value. For example, if among 5000 permutations 50 p-values were smaller than the observed p-value, then the adjusted p-value would be 50/5000 or 0.01.

All statistical analysis was performed using SAS and SAS/Genetics version 8.02 (SAS Inc, Cary, N.C.). Continuous variables were described as mean±standard deviation; categorical variables were described as percentages.

Results

Demographics and intraoperative characteristics of the 2104 study patients are presented in Table 14; with the exception of age and preoperative beta-adrenergic antagonist (beta blocker) therapy, there were no differences between those with or without stroke. Of the 2104 patients, 38 (1.8%) suffered in-hospital stroke. As not all SNPs were available in all patients, a subset of patients with complete clinical and genetic data was used for analysis. The final multivariabie genetic model included 1635 patients of whom 28 (1.7%) experienced stroke.

Figure 5:
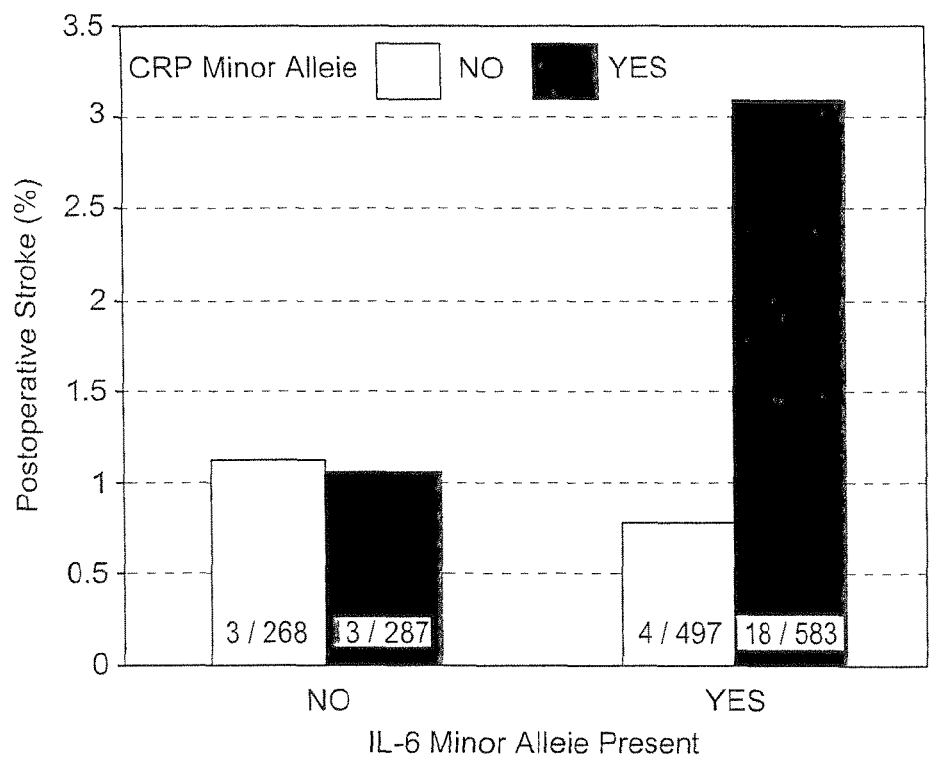
FIG. 5. The incidence of postoperative stroke in patients possessing the combination of single nucleotide polymorphisms (SNPs) in both C-reactive protein (CRP) (3'UTR 1846C/T) and interleukin-6 (IL6) (−174G/C). The combination of these SNPs significantly increased the risk of stroke (odds ratio 3.3, 95% CI 1.4-8.1; p=0.0023).

No single SNP alone was significantly associated with stroke. However, in paired tests, a SNP pair representing individuals having minor alleles for both CRP (3'UTR 1846C/T) and IL6 (−174G/C) was significantly associated with stroke. Of the 1635 patients, 583 (36%) had minor alleles for both of these SNPs. The incidence of stroke in patients with this genotype was 3.09% (18/583), compared to 0.95% (10/1052) in patients without this combination (OR 3.3, 95% CI 1.4-8.1; C-index=0.646; p=0.0023; FIG. 5). Thus, individuals with at least one minor allele at each locus were approximately three times more likely to have a stroke than patients without this combination. The two SNPs involved are among the nine in the inflammation category. After adjustment for multiple comparisons (involving 36 pairwise combinations) using permutation testing, the p-value for this combination of minor alleles remained significant (adjusted-p=0.023).

Due to the relatively few events (28 total strokes in 1635 patients), the number of additional terms that could be tested in a multivariable model were limited. However, as the stroke patients were older, a second model was constructed that, in addition to the identified SNPs, included age as a clinical covariable. That model was also highly significant (C-index=0.718, p=0.0001). Coefficients for age and genotype in this model demonstrated an odds ratio of 3.2 (p=0.0020, 95% CI=1.4-7.8) for the minor allele combination and 1.05 for each additional year of age (95% CI=1.02-1.10, 0.0057). This is not only consistent with prior investigations into risk factors of perioperative stroke (Newman et al, Circulation 94(9 Suppl):II74-II80 (1996)), but further emphasizes the value added by genotype information. When beta blocker therapy as a clinical covariable was tested, it became non-significant (p=0.5015) while the SNP combination remained significant (p=0.0034).

With regard to any gender or population structure effects, there was no association between stroke and gender (p=0.4933) nor between stroke and self-declared race (p=0.8258). Although several genotypes were distributed differentially among races, in the final multivariable genetic model, neither race nor gender were associated with stroke (p=0.2083 and p=0.6437, respectively; Table 17). Furthermore, the ethnic indicator variables from the population structure analysis were similarly non-significant when added to SNPs and age in the final multivariable model (p=0.1910).

TABLE 17

Race and Gender: Effects on stroke outcome and polymorphism associations

|  | No Stroke | Stroke | P-value* |
|---|---|---|---|
| Race |  |  | 0.208 |
| African American | 193 | 4 (2.0) |  |
| Caucasian | 1335 | 22 (1.6) |  |
| American Indian | 52 | 0 (0) |  |
| Hispanic | 5 | 0 (0) |  |
| Asian | 3 | 1 (25.0) |  |
| Other/Unknown | 19 | 1 (5.0) |  |
| Gender |  |  | 0.644 |
| Male | 1074 | 17 (1.6) |  |
| Female | 533 | 11 (2.0) |  |

*P-values represent significance level of race or gender with stroke in final multivariable model controlling for both age and genotype; percentage represented by parentheses ( ).

Summarizing, stroke following cardiac surgery is a relatively uncommon but potentially devastating event; the incidence of stroke in this so study (1.8%) was similar to that of other studies (Roach et al, N. Engl. J. Med. 335(25): 185701863 (1996), Bucerius et al, Arm Thorac. Surg. 75(2): 472-478 (2003), Ruel et al, Ann. Thorac. Surg. 78(1):77-83 (2004)). Previous investigations designed to understand risk factors associated with this adverse outcome have typically relied on clinical variables to construct risk indices (Newman et al, Circulation 94(9 Suppl):II74-II80 (1996)). Age, for example, is a robust risk factor for perioperative stroke and was reconfirmed in this present study (Newman et al, Circulation 94(9 Suppl):II74-II80 (1996)). A new significant relationship, independent of age, has now been demonstrated between stroke and an individual's genetic makeup. The present findings reveal that the concurrent presence of at least one minor allele at each of two loci (CRP: 3'UTR 1846C/T; IL6: −1740/C) is a risk factor for stroke, increasing risk more than three-fold.

The observation that the interaction of these two inflammatory SNPs contributes to perioperative stroke suggests that inflammatory pathways may be important mechanistic factors in either initiating or otherwise modulating stroke after cardiac surgery. This interpretation is consistent with current knowledge regarding CPB initiating and IL6 mediating a robust inflammatory response (Levy and Tanaka, Ann. Thorac. Surg. 75(2):S715-720 (2003)). no Such a finding is also consistent with the view that inflammation plays an important role in the etiology and propagation of cerebrovascular disease and stroke in the general population (Adams et al, BMC Med. Genet. 4(1):6 (2003), Humphries and Morgan, Lancet Neurol. 3(4):227-235 (2004)). Unexpectedly, thrombotic polymorphisms, significantly associated with stroke in non-cardiac surgery settings (Kahn, South Med. J. 96(4):350-353 (2003), Endler and Mannhalter, Clin., Chim. Acta 330(1-2):31-55 (2003)), were not shown to be related to stroke in this analysis, suggesting that inflammatory etiologies may supercede thrombotic causes of stroke in cardiac surgery patients.

The two individual inflammatory polymorphisms identified have been previously characterized outside the setting of cardiac surgery. The polymorphism involving the promoter region of the IL6 gene (−174G/C) has been shown to be an independent risk factor for lacunar stroke (Revilla et al, Neurosci. Lett. 324(1):29-32 (2002)). In addition to increasing the incidence of stroke, the same SNP has been shown to increase stroke severity worsening three month outcomes after ischemic stroke (Greisenegger et al, Thromb. Res. 110(4):181-186 (2003)). Interestingly, the IL6 SNP, when combined with a second inflammatory polymorphism (ICAM-1, 469E/K), appears to have an even greater effect on stroke risk. In a study by Pola et al., both IL6 and ICAM-1 SNPs were independently associated with stroke risk (OR 8.6 and 4.0, respectively), but when present together had a synergistic effect (OR, 10.1; 95% CI, 2.1-48.5) (Pola et al, Stroke 34(4):881-885 (2003)). Following cardiac surgery, the IL6 polymorphism is thought to influence plasma levels and functional activity of the IL6 protein and has been associated with other perioperative inflammatory complications (Gaudino et al, J. Thorac. Cardiovasc. Surg. 126(4):1107-1112 (2003), Gaudino et al, Circulation 108(Suppl 1):11195-11199 (2003), Burzotta et al, Am. J. Cardiol. 88(10):1125-1128 (2001)). However association between IL6 polymorphism and perioperative neurologic outcome has not been previously described.

C-reactive protein, an acute-phase reactant also indicating underlying inflammation, has repeatedly been shown to influence the risk of cardiovascular disease and stroke (Rost et al, Stroke 32(11):2575-2579 (2001), Curb et al, Circulation 107(15):2016-2020 (2003), Ford and Giles, Arterioscler. Thromb. Vasc. Biol. 20(4):1052-1056 (2000)). Indeed, Rost et al., demonstrated that elevated plasma CRP significantly predicts risk of stroke and transient ischemic attack in the elderly (Rost et al, Stroke 32(11):2575-2579 (2001)). The C/T polymorphism in the 3' UTR of the CRP gene has been associated with increased basal plasma levels of CRP and is part of a haplotype associated with elevated peak CRP levels after CABG (Russell et al, Hum. Mol. Genet. 13(1):137-147 (2004), Brull et al, Arterioscler Thromb. Vase. Biol. 23(11):2063-2069 (2003)). The mechanism by which this variant might influence CRP expression remains to be established, but it may involve alterations in the stability of the CRP mRNA which depend on the 3'UTR sequences (Murphy et al, J. Biol. Chem. 270(2):704-708 (1995)). By further increasing CRP levels, this polymorphism may increase the risk of stroke, although the precise mechanism by which CRP may act on stroke in this setting is not well understood (Cao et al, Circulation 108(2):166-170 (2003)).

Of particular interest is the finding that it is the interaction between IL6 and CRP SNPs, and not each individual SNP alone, that appears to be an important determinant of stroke risk after cardiac surgery. Epistasis, or the interaction between genes is a phenomenon of increasing interest in genetic epidemiology (Cordell, Hum. Mol. Genet, 11(20): 2463-2468 (2002)). A plausible biological model could be postulated for the epistasis event observed in the current study, as induction of the acute phase CRP response in hepatocytes is promoted by the synergistic action of pro-inflammatory cytokines IL6 and IL1β (Ganter et al, EMBO J. 8(12):3773-3779 (1989)). Therefore, genetic variants modulating IL6 levels and the expression of CRP may contribute to the perioperative pro-inflammatory phenotype seen in cardiac surgical patients.

There are some potential limitations to this study. Although the sample consisted of 2104 patients, limitations of multiplex genotyping resulted in missing genotypes for some SNPs in some patients. These data are missing at random with respect to patient characteristics and therefore would not be expected to bias tests of association. Population admixture is also a concern in genetic association studies since it can mask, or falsely identify, a phenotype with a genetic trait (Deng et al, J. Clin. Densitom. 4(4):353-361 (2001)). Importantly, no significant association of race to stroke was identified thereby minimizing this possible confounding effect. Lastly, although it is speculated that this unique gene combination may have mediated its stroke effect via changes in IL6 and CRP protein levels, these were not measured in the patients. However, these SNPs, at least individually, have been previously demonstrated in cardiac surgery patients to influence their respective protein levels (Burzotta et al, Am. J. Cardiol. 88(10):1125-1128 (2001), Brull et al, Arterioscler Thromb. Vasc. Biol. 23(11):2063-2069 (2003)).

The implications of these findings are several-fold. Understanding risk of stroke in cardiac surgery settings can facilitate informing patients of enhanced individual risk. Since this SNIP combination occurs in a large percentage of patients, 36% in the study described, such knowledge is important to many surgery patients. In addition, as new neuroprotective strategies and/or related pharmacologic agents become available, a more rational allocation of these likely higher cost therapies to the highest risk patients may be possible. In addition, identification of this unique polymorphism combination emphasizes the potentially significant effect that inflammation plays in cardiac surgery-related stroke. Identifying specific mechanisms whereby this SNP combination mediates its effects will be important in understanding targets whereby modulating perioperative inflammation might result in improvement in patient outcome after cardiac surgery.

All documents and other information sources cited above are hereby incorporated in their entirety by reference.

What is claimed is:

1. A method of treating a subject for perioperative or periprocedure bleeding comprising:

a) detecting the C allele of the $\alpha_2\beta_1$ integrin −52C/T polymorphism by contacting a biological sample containing nucleic acid from the subject with an oligonucleotide that hybridizes to the $\alpha_2\beta_1$ integrin gene and detecting the C allele using PCR, extension primer analysis, or mass spectrometry; and b) administering a biphasic antithrombotic therapy to the subject that preoperatively and/or perioperatively halts subclinical thrombosis and postoperatively prevents thrombotic complications.

2. A method of treating a subject for perioperative or periprocedure bleeding comprising:

a) detecting the C allele of the $\alpha_2\beta_1$ integrin −52C/T polymorphism by contacting a biological sample containing nucleic acid from the subject with an oligonucleotide that hybridizes to the $\alpha_2\beta_1$ integrin gene and detecting the C allele using PCR, extension primer analysis, or mass spectrometry; and
   b) administering to the subject a preoperative and/or postoperative therapy that reduces thrombin activation and bleeding, and/or more aggressive heparin dosing relative to a subject lacking the C allele of the $\alpha_2\beta_1$ integrin −52C/T polymorphism.

3. A method of treating a subject for perioperative or periprocedure bleeding comprising:
   administering a biphasic antithrombotic therapy that preoperatively and/or perioperatively halts subclinical thrombosis and postoperatively prevents thrombotic complications to a subject identified as having the C allele of the $\alpha_2\beta_1$ integrin −52C/T polymorphism.

4. A method of treating a subject for perioperative or periprocedure bleeding comprising:
   administering to a subject identified as having the C allele of the $\alpha_2\beta_1$ integrin −52C/T polymorphism, a) a preoperative and/or postoperative therapy that reduces thrombin activation and bleeding; and/or b) more aggressive heparin dosing relative to a subject lacking the C allele of the $\alpha_2\beta_1$ integrin −52C/T polymorphism.

* * * * *

UNITED STATES PATENT AND TRADEMARK OFFICE
CERTIFICATE OF CORRECTION

PATENT NO. : 9,556,486 B2
APPLICATION NO. : 14/099718
DATED : January 31, 2017
INVENTOR(S) : Schwinn et al.

Page 1 of 1

It is certified that error appears in the above-identified patent and that said Letters Patent is hereby corrected as shown below:

On the Title Page

Item (56) OTHER PUBLICATIONS: Please add the reference below:
Stafford-Smith et al., "Association of Genetic Polymorphisms With Risk of Renal Injury After Coronary Bypass Graft Surgery", American Journal of Kidney diseases 45(3):519-530 (2005)

In the Specification

Column 7, Line 36: Please correct "(SNFs)" to read -- (SNPs) --

Column 11, Line 61: Please correct "$\beta_2\beta_1$" to read -- $\alpha_2\beta_1$ --

Column 12, Line 30: "$\beta_2\beta_1$" to read -- $\alpha_2\beta_1$ --

Column 13, Line 45: Please correct "$\beta_2\beta_1$" to read -- $\alpha_2\beta_1$ --

Signed and Sealed this
Twenty-ninth Day of August, 2017

Joseph Matal
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 158

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
acgttggatg tggcctatta gcaccaaaac                                    30
```

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
acgttggatg agacatccca atatggtggg                                       30

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
acgttggatg atccactcaa ggctcccttg                                       30

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
acgttggatg ttggcagcag gagcagcaag                                       30

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
acgttggatg tgttgttagc cagactgagc                                       30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
acgttggatg aaggcaatga gctgaagacc                                       30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
acgttggatg ccttcagcag attctccttc                                       30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
acgttggatg ttgctggact tctctttggg                                    30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
acgttggatg atttcccagg aacctctgtg                                    30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
acgttggatg atacgctgtg caccagaatg                                    30

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
acgttggatg ttttgcacag ttttattctg                                    30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
acgttggatg agtcagtctt gcattttaat                                    30

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
acgttggatg tcttctaccc cacgaaggtc                                    30

<210> SEQ ID NO 14
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
acgttggatg attcccaccg cctttctcct g        31

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
acgttggatg taaaagtctg agggctaccg        30

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
acgttggatg aagcctgaca cctgcaatag        30

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
acgttggatg aaggaggcct aattaaaacc        30

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
acgttggatg cattgctata acaaattcac        30

<210> SEQ ID NO 19
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
acgttggatg ctgaaaggtt acttcaagga c        31

<210> SEQ ID NO 20

```
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
acgttggatg tgggctaata ggactacttc                                           30

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
acgttggatg ctcacagact aaatgaggcc                                           30

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
acgttggatg cacacaagtg aacagacaag                                           30

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
acgttggatg catttaagca acatcttccc                                           30

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
acgttggatg aacttcccat cattttgtcc                                           30

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
acgttggatg ctccgatgat acacggctga                                           30

<210> SEQ ID NO 26
<211> LENGTH: 30
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
acgttggatg aggttgttga cacaagagag                                    30

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
acgttggatg agtcacagtc ggtgccaatg                                    30

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
acgttggatg ggtaccttcg agtgcatctg                                    30

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
acgttggatg atgccttcac aaagcggaag                                    30

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
acgttggatg cttgaaggag aaggtgtctg                                    30

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ttaccttgca tattgaattg ctcc                                          24

<210> SEQ ID NO 32
<211> LENGTH: 18
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 32
ggctcccttg cccacagg                                                    18

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tccagcttgg gtgtgggc                                                    18

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tcacagcgag gtgagccc                                                    18

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
taccaacaga accaccttcc                                                  20

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ctgttaaaac aagtggttca gta                                              23

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ctaccccacg aaggtcaaga atac                                             24

<210> SEQ ID NO 38
<211> LENGTH: 23
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 38
ccgttggagg tctctcttag tga                                              23

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
aaagaaaaag aaagaagcag aga                                              23

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
aggacaaaat acctgtattc ct                                               22

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gaggcccatt ttccttcatt t                                                21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
aagcaacatc ttcccagcaa a                                                21

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gatacacggc tgactcccc                                                   19

<210> SEQ ID NO 44
<211> LENGTH: 23
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 44
cacagtcggt gccaatgtgg cgg                                            23

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gctgcgtgat gatgaaatcg                                                20

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ctggagacca ctcccatcct ttct                                           24

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gatgtggcca tcacattcgt cagat                                          25

<210> SEQ ID NO 48
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
acgttggatg tgtgacagga tggaagactg                                     30

<210> SEQ ID NO 49
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
acgttggatg gtggacgtag gtgttgaaag                                     30

<210> SEQ ID NO 50
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
acgttggatg attcctctgc agcacttcac                                           30

<210> SEQ ID NO 51
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
acgttggatg cggttcagtc cacataatgc                                           30

<210> SEQ ID NO 52
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
acgttggatg aaacggtcgc ttcgacgtgc                                           30

<210> SEQ ID NO 53
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
acgttggatg atccctttgg tgctcacgtg                                           30

<210> SEQ ID NO 54
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
acgttggatg agcctcaatg acgacctaag                                           30

<210> SEQ ID NO 55
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
acgttggatg gattgtgcaa tgtgacgtcc                                           30

<210> SEQ ID NO 56
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 56
acgttggatg acgccttgaa gtaactgcac                                           30

<210> SEQ ID NO 57
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
acgttggatg tcttctgtgt tctggctctc                                           30

<210> SEQ ID NO 58
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
acgttggatg acgccttgaa gtaactgcac                                           30

<210> SEQ ID NO 59
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
acgttggatg tcttctgtgt tctggctctc                                           30

<210> SEQ ID NO 60
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
acgttggatg gaaagatgtg cgctgatagg                                           30

<210> SEQ ID NO 61
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
acgttggatg cttgccacat ctctttctgc                                           30

<210> SEQ ID NO 62
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 62
acgttggatg gatttgtgtg taggaccctg                                    30

<210> SEQ ID NO 63
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
acgttggatg ggtccccaaa agaaatggag                                    30

<210> SEQ ID NO 64
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
acgttggatg ctcccagttc tagttctatc                                    30

<210> SEQ ID NO 65
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
acgttggatg ttgcctccat ttcttttggg                                    30

<210> SEQ ID NO 66
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
acgttggatg tgtccaagga gctgcaggc                                     29

<210> SEQ ID NO 67
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
acgttggatg tcggtgctct ggccgagcat                                    30

<210> SEQ ID NO 68
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
```
acgttggatg acattcccct tccacgcttg                               30

<210> SEQ ID NO 69
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
acgttggatg tagaggtctt ttgaccaccc                               30

<210> SEQ ID NO 70
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
aagactggct gctccctga                                           19

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
gcacttcact accaaatgag c                                        21

<210> SEQ ID NO 72
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
gctgcaggcc ccagatga                                            18

<210> SEQ ID NO 73
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
tttcccccta gttgtgtctt gc                                       22

<210> SEQ ID NO 74
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
caggcagtct acaacagcc                                                19

<210> SEQ ID NO 75
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
aagtaactgc acgaaatttg agg                                           23

<210> SEQ ID NO 76
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gggagggatg gagagaaaaa aac                                           23

<210> SEQ ID NO 77
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
accctggagg ctgaaccccg tcc                                           23

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
ttcctgcatc ctgtctggaa                                               20

<210> SEQ ID NO 79
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
gcggacatgg aggacgtg                                                 18

<210> SEQ ID NO 80
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
gaatggagga gggtgtctg                                                19

<210> SEQ ID NO 81
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
acgttggatg tggaaccaat cccgtgaaag                                30

<210> SEQ ID NO 82
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
acgttggatg agagagctgc ccatgaatag                                30

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
ccaataaaag tgactctcag c                                         21

<210> SEQ ID NO 84
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
acgttggatg tcttctaccc cacgaaggtc                                30

<210> SEQ ID NO 85
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
acgttggatg attcccaccg cctttctcct g                              31

<210> SEQ ID NO 86
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
ctaccccacg aaggtcaaga atac                                      24

<210> SEQ ID NO 87
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
acgttggatg ttttgcacag ttttattctg                              30

<210> SEQ ID NO 88
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
acgttggatg agtcagtctt gcattttaat                              30

<210> SEQ ID NO 89
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
ctgttaaaac aagtggttca gta                                     23

<210> SEQ ID NO 90
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
acgttggatg ctgaaaggtt acttcaagga c                            31

<210> SEQ ID NO 91
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
acgttggatg tgggctaata ggactacttc                              30

<210> SEQ ID NO 92
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
aggacaaaat acctgtattc ct                                      22

```
<210> SEQ ID NO 93
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
acgttggatg catttaagca acatcttccc                                    30

<210> SEQ ID NO 94
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
acgttggatg aacttcccat cattttgtcc                                    30

<210> SEQ ID NO 95
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
aagcaacatc ttcccagcaa a                                             21

<210> SEQ ID NO 96
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
acgttggatg gcttatgttt tctgacaatg                                    30

<210> SEQ ID NO 97
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
acgttggatg tcatagaata gggtatgaat                                    30

<210> SEQ ID NO 98
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
cataattcta tttcaaaagg ggc                                           23

<210> SEQ ID NO 99
```

```
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
acgttggatg ctcacagact aaatgaggcc                                        30

<210> SEQ ID NO 100
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
acgttggatg cacacaagtg aacagacaag                                        30

<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
gaggcccatt ttccttcatt t                                                 21

<210> SEQ ID NO 102
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
acgttggatg atgcccacct tcagacaaag                                        30

<210> SEQ ID NO 103
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
acgttggatg cctctgtgtc aaccatgttc                                        30

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
gagctcaaaa gctccctgag                                                   20

<210> SEQ ID NO 105
<211> LENGTH: 30
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
acgttggatg atccactcaa ggctcccttg                                          30

<210> SEQ ID NO 106
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
acgttggatg ttggcagcag gagcagcaag                                          30

<210> SEQ ID NO 107
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
ggctcccttg cccacagg                                                       18

<210> SEQ ID NO 108
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
acgttggatg tgttgttagc cagactgagc                                          30

<210> SEQ ID NO 109
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
acgttggatg aaggcaatga gctgaagacc                                          30

<210> SEQ ID NO 110
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
tccagcttgg gtgtgggc                                                       18

<210> SEQ ID NO 111
<211> LENGTH: 30
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 111
acgttggatg tggcctatta gcaccaaaac                                         30

<210> SEQ ID NO 112
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
acgttggatg agacatccca atatggtggg                                         30

<210> SEQ ID NO 113
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
ttaccttgca tattgaattg ctcc                                               24

<210> SEQ ID NO 114
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
acgttggatg gatccggtgt ttgcggaatc                                         30

<210> SEQ ID NO 115
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
acgttggatg agggaaaagt ttctgggcag                                         30

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
cggaatcagg aggggcgggc                                                    20

<210> SEQ ID NO 117
<211> LENGTH: 30
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 117
acgttggatg ccttcagcag attctccttc                                          30

<210> SEQ ID NO 118
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
acgttggatg ttgctggact tctctttggg                                          30

<210> SEQ ID NO 119
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
tcacagcgag gtgagccc                                                       18

<210> SEQ ID NO 120
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
acgttggatg ctccgatgat acacggctga                                          30

<210> SEQ ID NO 121
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
acgttggatg aggttgttga cacaagagag                                          30

<210> SEQ ID NO 122
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
gatacacggc tgactcccc                                                      19

<210> SEQ ID NO 123
<211> LENGTH: 30
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 123
acgttggatg aaggaaacag gagaccaacg                                              30

<210> SEQ ID NO 124
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
acgttggatg gaggataaag gacaagctgc                                              30

<210> SEQ ID NO 125
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
gaccaacgtg taagtttcac ttc                                                     23

<210> SEQ ID NO 126
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
acgttggatg gccatcttgt ttgccacatg                                              30

<210> SEQ ID NO 127
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
acgttggatg gtttgtcaat cccttggctc                                              30

<210> SEQ ID NO 128
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
ttgtttgcca catggagaga gact                                                    24

<210> SEQ ID NO 129
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 129
acgttggatg gaaatgtgaa catgtgggac                                      30

<210> SEQ ID NO 130
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
acgttggatg aggacattag gactgaaggg                                      30

<210> SEQ ID NO 131
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
tgtgaacatg tgggactttg tgct                                            24

<210> SEQ ID NO 132
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
acgttggatg agcctcaatg acgacctaag                                      30

<210> SEQ ID NO 133
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
acgttggatg gattgtgcaa tgtgacgtcc                                      30

<210> SEQ ID NO 134
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
tttcccccta gttgtgtctt gc                                              22

<210> SEQ ID NO 135
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 135
acgttggatg acgccttgaa gtaactgcac                              30

<210> SEQ ID NO 136
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
acgttggatg tcttctgtgt tctggctctc                              30

<210> SEQ ID NO 137
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
caggcagtct acaacagcc                                          19

<210> SEQ ID NO 138
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
acgttggatg acgccttgaa gtaactgcac                              30

<210> SEQ ID NO 139
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
acgttggatg tcttctgtgt tctggctctc                              30

<210> SEQ ID NO 140
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
aagtaactgc acgaaatttg agg                                     23

<210> SEQ ID NO 141
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 141
acgttggatg gaaagatgtg cgctgatagg                                                                30

<210> SEQ ID NO 142
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
acgttggatg cttgccacat ctctttctgc                                                                30

<210> SEQ ID NO 143
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
gggagggatg gagagaaaaa aac                                                                       23

<210> SEQ ID NO 144
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
acgttggatg gatttgtgtg taggaccctg                                                                30

<210> SEQ ID NO 145
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
acgttggatg ggtccccaaa agaaatggag                                                                30

<210> SEQ ID NO 146
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
accctggagg ctgaaccccg tcc                                                                       23

<210> SEQ ID NO 147
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147

```
acgttggatg ctcccagttc tagttctatc                                          30

<210> SEQ ID NO 148
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
acgttggatg ttgcctccat ttcttttggg                                          30

<210> SEQ ID NO 149
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
ttcctgcatc ctgtctggaa                                                     20

<210> SEQ ID NO 150
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
acgttggatg acacaaatca gtcagtggcc                                          30

<210> SEQ ID NO 151
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
acgttggatg atcaaggata cccctcacac                                          30

<210> SEQ ID NO 152
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
gaagaccccc ctcggaatc                                                      19

<210> SEQ ID NO 153
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
```

```
acgttggatg tgtccaagga gctgcaggc                                    29

<210> SEQ ID NO 154
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
acgttggatg tcggtgctct ggccgagcat                                   30

<210> SEQ ID NO 155
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
gcggacatgg aggacgtg                                                18

<210> SEQ ID NO 156
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
acgttggatg acattcccct tccacgcttg                                   30

<210> SEQ ID NO 157
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
acgttggatg tagaggtctt ttgaccaccc                                   30

<210> SEQ ID NO 158
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
gaatggagga gggtgtctg                                               19
```